(12) United States Patent
Nair et al.

(10) Patent No.: US 7,462,634 B2
(45) Date of Patent: Dec. 9, 2008

(54) N-(PYRIDIN-2-YL)-SULFONAMIDE DERIVATIVES

(75) Inventors: Sajiv Krishnan Nair, Vista, CA (US);
Michael Siu, San Diego, CA (US);
Wendy Dianne Taylor, San Diego, CA (US)

(73) Assignees: Agouron Pharmaceuticals, Inc., San Diego, CA (US); Pfizer Inc, New York, NY (US)

( * ) Notice: Subject to any disclaimer, the term of this patent is extended or adjusted under 35 U.S.C. 154(b) by 105 days.

(21) Appl. No.: 11/455,065

(22) Filed: Jun. 15, 2006

(65) Prior Publication Data

US 2007/0072914 A1    Mar. 29, 2007

Related U.S. Application Data

(60) Provisional application No. 60/748,778, filed on Dec. 9, 2005, provisional application No. 60/691,350, filed on Jun. 16, 2005.

(51) Int. Cl.
*C07D 213/72* (2006.01)
*C07D 417/02* (2006.01)
*A61K 31/44* (2006.01)

(52) U.S. Cl. .................... 514/342; 514/352; 546/269.7; 546/312

(58) Field of Classification Search ............. 546/269.7, 546/312; 514/342, 352
See application file for complete search history.

(56) References Cited

U.S. PATENT DOCUMENTS

| 2003/0166689 A1 | 9/2003 | Kurz et al. |
|---|---|---|
| 2005/0148631 A1 | 7/2005 | Cheng et al. |
| 2005/0282802 A1 | 12/2005 | Kostik et al. |
| 2006/0009455 A1 | 1/2006 | Corte et al. |
| 2006/0063779 A1 | 3/2006 | Gunzner et al. |
| 2006/0074237 A1 | 4/2006 | Amrein et al. |

FOREIGN PATENT DOCUMENTS

| DE | 2312728 | 3/1973 |
|---|---|---|
| EP | 0 682 016 | 11/1995 |
| WO | 03/099773 | 12/2003 |
| WO | 2005/060963 | 7/2005 |
| WO | WO2006014012 | 2/2006 |
| WO | WO2006024779 | 3/2006 |
| WO | WO2006034440 | 3/2006 |

OTHER PUBLICATIONS

PCT International Search Report, PCT/IB2006/001581.

*Primary Examiner*—Zinna N Davis
(74) *Attorney, Agent, or Firm*—Elsa Djuardi; John H. Engelmann

(57) ABSTRACT

The present invention relates to novel compounds, to pharmaceutical compositions comprising the compounds described herein, their pharmaceutically acceptable salts, hydrates and solvates, as well as to the use of the compounds in medicine and for the preparation of a medicament which acts on the human 11-β-hydroxysteroid dehydrogenase type 1 enzyme (11βHSD1).

11 Claims, No Drawings

N-(PYRIDIN-2-YL)-SULFONAMIDE DERIVATIVES

This application claims the benefit of U.S. Provisional Application No. 60/691,350 filed Jun. 16, 2005, and U.S. Provisional Application No. 60/748,778 filed Dec. 9, 2005, the contents of which are hereby incorporated by reference in their entireties.

FIELD OF THE INVENTION

The present invention relates to novel compounds, to pharmaceutical compositions comprising the compounds, as well as to the use of the compounds in medicine and for the preparation of a medicament which acts on the human 11-β-hydroxysteroid dehydrogenase type 1 enzyme (11βHSD1).

BACKGROUND OF THE INVENTION

It has been known for more than half a century that glucocorticoids have a central role in diabetes. For example, the removal of the pituitary or the adrenal gland from a diabetic animal alleviates the most severe symptoms of diabetes and lowers the concentration of glucose in the blood (Long, C. D. and F. D. W. Leukins (1936) *J. Exp. Med.* 63: 465-490; Houssay, B. A. (1942) *Endocrinology* 30: 884-892). Additionally, it is also well established that glucocorticoids enable the effect of glucagon on the liver. The role of 11βHSD1 as an important regulator of local glucocorticoid effects and thus of hepatic glucose production is well substantiated (see e.g. Jamieson et al. (2000) *J. Endocrinol.* 165: p. 685-692). The hepatic insulin sensitivity was improved in healthy human volunteers treated with the non-specific 11βHSD1 inhibitor carbenoxolone (Walker, B. R., et al. (1995) *J. Clin. Endocrinol. Metab.* 80: 3155-3159). Furthermore, the expected mechanism has been established by different experiments with mice and rats. These studies showed that the mRNA levels and activities of two key enzymes in hepatic glucose production were reduced, namely the rate-limiting enzyme in gluconeogenesis, phosphoenolpyruvate carboxykinase (PEPCK), and glucose-6-phosphatase (G6Pase) catalyzing the last common step of gluconeogenesis and glycogenolysis. Finally, the blood glucose level and hepatic glucose production was reduced in mice having the 11βHSD1 gene knocked-out. Data from this model also confirms that inhibition of 11βHSD1 will not cause hypoglycemia, as predicted, since the basal levels of PEPCK and G6Pase are regulated independently of glucocorticoids (Kotelevtsev, Y., et al., (1997) *Proc. Natl. Acad. Sci.* USA 94: 14924-14929).

Abdominal obesity is closely associated with glucose intolerance, hyperinsulinemia, hypertriglyceridemia, and other factors of the so-called Metabolic Syndrome (e.g. raised blood pressure, decreased levels of HDL and increased levels of VLDL) (Montague & O'Rahilly, *Diabetes* 49: 883-888, 2000). Obesity is an important factor in Metabolic Syndrome as well as in the majority (>80%) of type 2 diabetic, and omental fat appears to be of central importance. Inhibition of the enzyme in pre-adipocytes (stromal cells) has been shown to decrease the rate of differentiation into adipocytes. This is predicted to result in diminished expansion (possibly reduction) of the omental fat depot, i.e. reduced central obesity (Bujalska, I. J., Kumar, S., and Stewart, P. M. (1997) *Lancet* 349: 1210-1213).

SUMMARY OF THE INVENTION

The compounds of the present invention are useful as 11βHSD1 inhibitors.

In one aspect, the present invention provides compounds of formula (I):

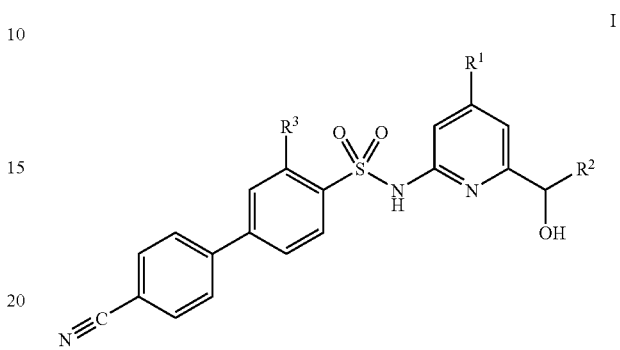

I wherein
$R^1$ is H or $(C_1\text{-}C_4)$alkyl;
$R^2$ is H or $(C_1\text{-}C_4)$alkyl;
$R^3$ is H, halo, $(C_1\text{-}C_6)$alkyl or $(C_1\text{-}C_6)$alkoxy;
or the pharmaceutically acceptable salts thereof.

In one embodiment, the invention is directed to said compounds of formula (I) or a pharmaceutically acceptable salt thereof, wherein $R^1$ is H. In a further embodiment, the invention is directed to said compounds of formula (I) or a pharmaceutically acceptable salt thereof, wherein $R^3$ is H or $CH_3$. In a still further embodiment, the invention is directed to said compounds of formula (I) or a pharmaceutically acceptable salt thereof, wherein $R^2$ is $-CH_2CH_3$.

In another embodiment, the invention is directed to said compounds of formula (I) or a pharmaceutically acceptable salt thereof, which are chiral. Preferably, the (+) enantiomer.

In another aspect, the invention provides compounds of formula I, selected from the group:

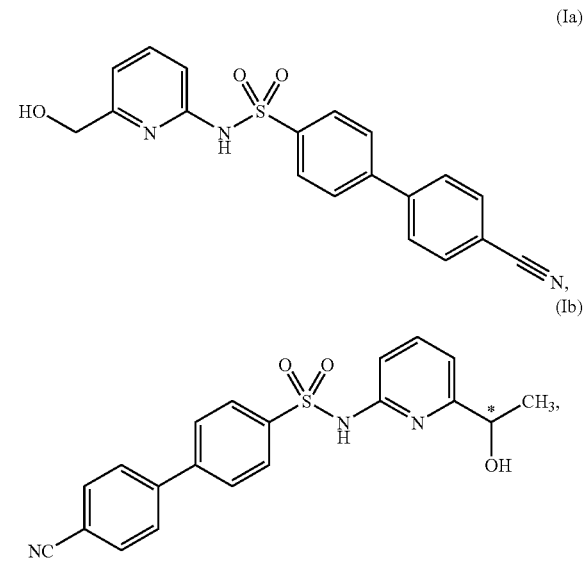

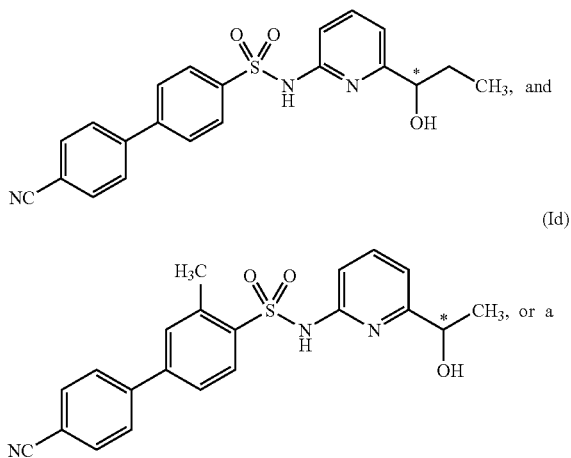

pharmaceutically acceptable salt thereof.

In another embodiment, the invention is directed to said compounds of formula (Ib), (Ic), (Id), or a pharmaceutically acceptable salt thereof, wherein each of which is the (+) enantiomer.

In a further aspect, the invention provides a compound having the formula II

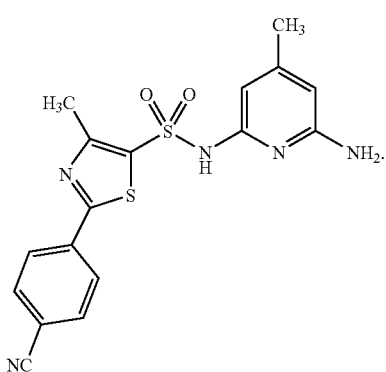

or a pharmaceutically acceptable salt thereof.

In another aspect, the invention provides a pharmaceutical composition comprising an effective amount of any of the above compounds of formulae I or II, or the pharmaceutically acceptable salts thereof, and a pharmaceutically acceptable carrier.

In another aspect, the invention provides a method for treating a disease, condition or disorder which would benefit by treatment with a 11βHSD1 inhibitor (such as type 2 diabetes) comprising administering to a mammal an effective amount of any of the above compounds of formula I or II, or the pharmaceutically acceptable salts thereof.

In another aspect, the invention provides methods for treating metabolic syndrome, insulin resistance syndrome, obesity, glaucoma, hyperlipidemia, hyperglycemia, hyperinsulinemia, osteoporosis, atherosclerosis, dementia, depression, or diseases in which the liver is a target organ, wherein the method comprises administering to a mammal an effective amount of any of the above compounds of formulae I or II, or the pharmaceutically acceptable salts thereof. In another aspect, the invention provides methods for treating glaucoma comprising administering to a mammal an effective amount of any of the above compounds of formulae I or II, or the pharmaceutically acceptable salts thereof, in combination with a prostanoid receptor agonist, wherein said agonist is latanoprost, bimatoprost, travaprost, or unoprost.

In another aspect, the invention provides for a compound of formula I or II, or a pharmaceutically acceptable salt thereof, for use as a medicament.

In another aspect, the invention provides for the use of a compound of formula I or II, or a pharmaceutically acceptable salt thereof, in the manufacture of a medicament for the treatment of a disease, condition or disorder which would benefit by treatment with a 11βHSD1 inhibitor (such as type 2 diabetes).

DEFINITIONS

As used herein, the terms "comprising" and "including" are used in their open, non-limiting sense.

As used herein, the term "alkyl," unless otherwise indicated, refers to saturated monovalent hydrocarbon radicals having straight or branched moieties. As used herein, the term "alkenyl," unless otherwise indicated, refers to alkyl moieties having at least one carbon-carbon double bond wherein alkyl is as defined above and including E and Z isomers of said alkenyl moiety.

As used herein, the term "alkynyl," unless otherwise indicated, refers to alkyl moieties having at least one carbon-carbon triple bond wherein alkyl is as defined above. As used herein, the term "alkoxy," unless otherwise indicated, refers to O-alkyl groups wherein alkyl is as defined above.

As used herein, the term "amino," unless otherwise indicated, refers to the —$NH_2$ radical and any substitutions of the N atom.

As used herein, the terms "halogen" and "halo," unless otherwise indicated, refers to fluorine, chlorine, bromine and/or iodine.

As used herein, the term "trifluoromethyl," unless otherwise indicated, refers to a —$CF_3$ group.

As used herein, the term "trifluoromethoxy," unless otherwise indicated, refers to a —$OCF_3$ group.

As used herein, the term "cyano," unless otherwise indicated, refers to a —CN group.

As used herein, the term, "Ms," unless otherwise indicated, refers to methanesulfonate (—$SO_2CH_3$).

As used herein, the term "Me," unless otherwise indicated, refers to methyl.

As used herein, the term "MeOH," unless otherwise indicated, refers to methanol.

As used herein, the term "Et," unless otherwise indicated, refers to ethyl.

As used herein, the term "$Et_2O$," unless otherwise indicated, refers to diethylether.

As used herein, the term "EtOH," unless otherwise indicated, refers to ethanol.

As used herein, the term "$Et_3N$," unless otherwise indicated, refers to triethylamine.

As used herein, the term "TEA," unless otherwise indicated, refers to triethylamine.

As used herein, the term "EtOAc," unless otherwise indicated, refers to ethyl acetate.

As used herein, the term "$AlMe_2Cl$," unless otherwise indicated, refers to dimethyl aluminum chloride.

As used herein, the term "Ac," unless otherwise indicated, refers to acetyl.

As used herein, the term "TFA," unless otherwise indicated, refers to trifluoroacetic acid.

As used herein, the term "HATU," unless otherwise indicated, refers to N, N,N',N'-tetramethyluronium hexafluorophosphate.

As used herein, the term "THF," unless otherwise indicated, refers to tetrahydrofuran.

As used herein, the term "TlOH," unless otherwise indicated, refers to thallium(I) hydroxide.

As used herein, the term "TlOEt," unless otherwise indicated, refers to thallium(I) ethoxide.

As used herein, the term "PCy$_3$," unless otherwise indicated, refers to tricyclohexylphosphine.

As used herein, the term "Pd$_2$(dba)$_3$," unless otherwise indicated, refers to tris(dibenzylideneacetone)dipalladium (0).

As used herein, the term "Pd(OAc)$_2$," unless otherwise indicated, refers to palladium(II) acetate.

As used herein, the term "Pd(PPh$_3$)$_2$Cl$_2$," unless otherwise indicated, refers to dichlorobis(triphenylphosphine)palladium(II).

As used herein, the term "Pd(PPh$_3$)$_4$," unless otherwise indicated, refers to tetrakis(triphenylphophine)palladium(0).

As used herein, the term "Pd(dppf)Cl$_2$," unless otherwise indicated, refers to (1,1'-bis(diphenylphosphino)-ferrocene) dichloropalladium(II), complex with dichloromethane (1:1).

As used herein, the term "G6P," unless otherwise indicated, refers to glucose-6-phosphate.

As used herein, the term "NIDDM," unless otherwise indicated, refers to non insulin dependent diabetes mellitus.

As used herein, the term "NADPH," unless otherwise indicated, refers to nicotinamide adenine dinucleotide phosphate reduced form.

As used herein, the term "CDCl$_3$ or CHLORFORM-D," unless otherwise indicated, refers to deuterochloroform.

As used herein, the term "CD$_3$OD," unless otherwise indicated, refers to deuteromethanol.

As used herein, the term "CD$_3$CN," unless otherwise indicated, refers to deuteroacetonitrile.

As used herein, the term "DEAD," unless otherwise indicated, refers to diethyl azodicarboxylate.

As used herein, the term "TsCH$_2$NC," unless otherwise indicated, refers to tosylmethyl isocyanide.

As used herein, the term "ClSO$_3$H," unless otherwise indicated, refers to chlorosulfonic acid.

As used herein, the term "DMSO-d$_6$ or DMSO-D$_6$," unless otherwise indicated, refers to deuterodimethyl sulfoxide.

As used herein, the term "DME," unless otherwise indicated, refers to 1,2-dimethoxyethane.

As used herein, the term "DMF," unless otherwise indicated, refers to N,N-dimethylformamide.

As used herein, the term "DMSO," unless otherwise indicated, refers to dimethylsulfoxide.

As used herein, the term "DIPEA," unless otherwise indicated, refers to diisopropylethylamine.

As used herein, the term "DI," unless otherwise indicated, refers to deionized.

As used herein, the term "KOAc," unless otherwise indicated, refers to potassium acetate.

As used herein, the term "neat," unless otherwise indicated, refers to an absence of solvent.

As used herein, the term "mmol," unless otherwise indicated, refers to millimole.

As used herein, the term "equiv," unless otherwise indicated, refers to equivalent.

As used herein, the term "mL," unless otherwise indicated, refers to milliliter.

As used herein, the term "U," unless otherwise indicated, refers to units.

As used herein, the term "mm," unless otherwise indicated, refers to millimeter.

As used herein, the term "g," unless otherwise indicated, refers to gram.

As used herein, the term "kg," unless otherwise indicated, refers to kilogram.

As used herein, the term "h," unless otherwise indicated, refers to hour.

As used herein, the term "min," unless otherwise indicated, refers to minute.

As used herein, the term "µL," unless otherwise indicated, refers to microliter.

As used herein, the term "µM," unless otherwise indicated, refers to micromolar.

As used herein, the term "µm," unless otherwise indicated, refers to micrometer.

As used herein, the term "M," unless otherwise indicated, refers to molar.

As used herein, the term "N," unless otherwise indicated, refers to normal.

As used herein, the term "nm," unless otherwise indicated, refers to nanometer.

As used herein, the term "nM," unless otherwise indicated, refers to nanoMolar.

As used herein, the term "amu," unless otherwise indicated, refers to atomic mass unit.

As used herein, the term "° C.," unless otherwise indicated, refers to Celsius.

As used herein, the term "m/z," unless otherwise indicated, refers to mass/charge ratio.

As used herein, the term "wt/wt," unless otherwise indicated, refers to weight/weight.

As used herein, the term "v/v," unless otherwise indicated, refers to volume/volume.

As used herein, the term "mL/min," unless otherwise indicated, refers to milliliter/minute.

As used herein, the term "UV," unless otherwise indicated, refers to ultraviolet.

As used herein, the term "APCl-MS," unless otherwise indicated, refers to atmospheric pressure chemical ionization mass spectroscopy.

As used herein, the term "HPLC," unless otherwise indicated, refers to high performance liquid chromatograph.

As used herein, the term "LC," unless otherwise indicated, refers to liquid chromatograph.

As used herein, the term "LCMS," unless otherwise indicated, refers to liquid chromatography mass spectroscopy.

As used herein, the term "SFC," unless otherwise indicated, refers to supercritical fluid chromatography.

As used herein, the term "sat," unless otherwise indicated, refers to saturated.

As used herein, the term "aq," unless otherwise indicated, refers to aqueous.

As used herein, the term "ELSD," unless otherwise indicated, refers to evaporative light scattering detection.

As used herein, the term "MS," unless otherwise indicated, refers to mass spectroscopy.

As used herein, the term "HRMS (ESI)," unless otherwise indicated, refers to high resolution mass spectrometry (electrospray ionization).

As used herein, the term "Anal.," unless otherwise indicated, refers to analytical.

As used herein, the term "Calcd," unless otherwise indicated, refers to calculated.

As used herein, the term "NT," unless otherwise indicated, refers to not tested.

As used herein, the term "NA," unless otherwise indicated, refers to not tested.

As used herein, the term "RT," unless otherwise indicated, refers to room temperature.

As used herein, the term "Mth.," unless otherwise indicated, refers to method.

As used herein, the term "Celite®," unless otherwise indicated, refers to a white solid diatomite filter agent commercially available from World Minerals located in Los Angeles, Calif. USA.

As used herein, the term "$K_i$," unless otherwise indicated, refers to values of enzyme inhibition constant.

As used herein, the term "$K_i$app," unless otherwise indicated, refers to the apparent $K_i$.

As used herein, the term "$IC_{50}$," unless otherwise indicated, refers to concentrations required for at least 50% enzyme inhibition.

As used herein, the term "substituted," unless otherwise indicated, refers to that the specified group or moiety bears one or more substituents. The term "unsubstituted," means that the specified group bears no substituents.

As used herein, the term "optionally substituted," unless otherwise indicated, refers to that the specified group is unsubstituted or substituted by one or more substituents.

In accordance with convention, in some structural formula herein, the carbon atoms and their bound hydrogen atoms are not explicitly depicted e.g., 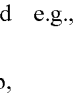 represents a methyl group, 

represents an ethyl group,

represents a cyclopentyl group, etc.

As used herein, the term "cycloalkyl," unless otherwise indicated, refers to a non-aromatic, saturated or partially saturated, monocyclic or fused, spiro or unfused bicyclic or tricyclic hydrocarbon referred to herein containing a total of from 3 to 10 carbon atoms, suitably 5-8 ring carbon atoms. Exemplary cycloalkyls include rings having from 3-10 carbon atoms, such as cyclopropyl, cyclobutyl, cyclopentyl, cyclohexyl, cycloheptyl, and adamantyl.

As used herein, the term "aryl" or "$(C_6-C_{10})$aryl," unless otherwise indicated, refers to an organic radical derived from an aromatic hydrocarbon by removal of one hydrogen, such as phenyl or naphthyl.

As used herein, the term "heteroaryl" or "(5-10)-membered heteroaryl," unless otherwise indicated, refers to aromatic groups containing one to four heteroatoms each selected from O, S and N, wherein each heteroaryl group has from 5-10 atoms, respectively, in its ring system, and with the proviso that the ring of said group does not contain two adjacent O or S atoms. The heteroaryl groups include benzo-fused ring systems. An example of a 5 membered heterocyclic group is thiazolyl, an example of a 7 membered ring is azepinyl, and an example of a 10 membered heterocyclic group is quinolinyl. Other examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Unless otherwise indicated, the term "oxo" refers to =O.

As used herein, the compounds of the invention are intended to include solvates, hydrates and pharmaceutically acceptable salts of the compounds of formulae I and II and their specific embodiments.

As used herein, "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

As used herein, the phrase "pharmaceutically acceptable salt(s)," unless otherwise indicated, includes salts of acidic or basic groups which may be present in the claimed compounds. The claimed compounds that are basic in nature are capable of forming a wide variety of salts with various inorganic and organic acids. Further description of the salts of the invention are described below.

As used herein, the term "diseases in which the liver is a target organ," unless otherwise indicated means diabetes, hepatitis, liver cancer, liver fibrosis, and malaria.

As used herein, the term "metabolic syndrome", as used herein, unless otherwise indicated means psoriasis, diabetes mellitus, wound healing, inflammation, neurodegenerative diseases, galactosemia, maple syrup urine disease, phenylketonuria, hypersarcosinemia, thymine uraciluria, sulfinuria, isovaleric acidemia, saccharopinuria, 4-hydroxybutyric aciduria, glucose-6-phosphate dehydrogenase deficiency, and pyruvate dehydrogenase deficiency.

As used herein, the term "treating," unless otherwise indicated refers to reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, the term "modulate" or "modulating," refers to the ability of a modulator for a member of the steroid/thyroid superfamily to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control.

As used herein, the phrase "ophthalmic diseases", unless otherwise indicated, refers to diseases of the eye including but not limited to glaucoma, age related macular degeneration (AMD) including exudative (wet AMD) and non-exudative (dry AMD), choroidal neovascularization, retinopathies such as diabetic retinopathy, retinitis pigmentosa and retinopathy of prematurity, diabetic macular edema, retinitis, uveitis, cystoid macular edema and other diseases or conditions of the eye.

As used herein, the term "obesity" or "obese," refers generally to individuals who are at least about 20-30% over the average weight for his/her age, sex and height. Technically, "obese" is defined, for males, as individuals whose body mass index is greater than 27.8 kg/m², and for females, as individuals whose body mass index is greater than 27.3 kg/m². Those of skill in the art readily recognize that the invention method is not limited to those who fall within the above criteria. Indeed, the method of the invention can also be advantageously practiced by individuals who fall outside of these traditional criteria, for example, by those who may be prone to obesity.

As used herein, the term "inflammatory disorders," unless otherwise indicated, refers to disorders such as rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

As used herein, the phrase "therapeutically effective amount," unless otherwise indicated, refers to that amount of drug or pharmaceutical agent that will elicit the biological or medical response of a tissue, system, animal, or human that is being sought by a researcher, veterinarian, medical doctor or other.

As used herein, the phrase "amount . . . effective to lower blood glucose levels," unless otherwise indicated, refers to levels of compound sufficient to provide circulating concentrations high enough to accomplish the desired effect. Such a concentration typically falls in the range of about 10 nM up to 2 μM; with concentrations in the range of about 100 nM up to 500 nM being preferred. As noted previously, since the activity of different compounds as set forth above may vary considerably, and since individual subjects may present a wide variation in severity of symptoms, it is up to the practitioner to determine a subject's response to treatment and vary the dosages accordingly.

As used herein, the phrase "insulin resistance," unless otherwise indicated, refers to the reduced sensitivity to the actions of insulin in the whole body or individual tissues, such as skeletal muscle tissue, myocardial tissue, fat tissue or liver tissue. Insulin resistance occurs in many individuals with or without diabetes mellitus.

As used herein, the phrase "insulin resistance syndrome", unless otherwise indicated, refers to the cluster of manifestations that include insulin resistance, hyperinsulinemia, NIDDM, arterial hypertension, central (visceral) obesity, and dyslipidemia.

As used herein, the term "(+) enantiomer", unless otherwise indicated, refers to the conventions used for naming chiral compounds, based on the compounds' ability to rotate polarized light.

Certain functional groups contained within the compounds of the present invention can be substituted for bioisosteric groups, that is, groups that have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein. Isotopically labeled compounds of this invention can generally be prepared by carrying out the procedures disclosed in the Schemes and/or in the Examples below, by substituting a readily available isotopically labeled reagent for a non-isotopically labeled reagent.

Other aspects, advantages, and features of the invention will become apparent from the detailed description below.

DETAILED DESCRIPTION OF THE INVENTION

The following Schemes illustrate the preparation of the compounds of the present invention.

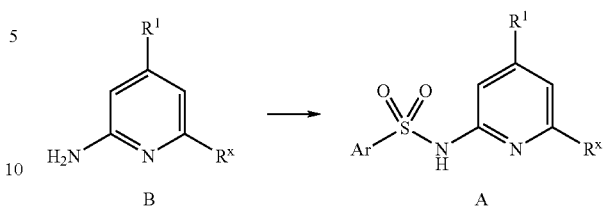

Scheme 1

Referring to Scheme 1 above, the compound of formula A may be prepared by reacting a compound of formula B with an Ar-sulfonyl halide, Ar-sulfinyl halide, or Ar-sulfinate in the presence of a suitable base such as an amine in a suitable solvent. Suitable bases include pyridine, triethylamine, and diisopropylethylamine. Suitable solvents include pyridine, dichloromethane, or THF. The aforementioned reaction can be conducted at about room temperature (about 20° C.) or heated for an appropriate time period, such as 2 hours to 16 hours, depending on the solvent system used. After the reaction is substantially completed, the base may be removed in vacuo and the resulting residue may be purified using conventional purification techniques.

Any of the above compounds of formula I can be converted into other analogous compound by standard chemical manipulations. All starting materials, reagents, and solvents are commercially available and are known to those of skill in the art unless otherwise stated. These chemical manipulations are known to those skilled in the art and include (a) removal of a protecting group by methods outlined in T. W. Greene and P.G.M. Wuts, "Protective Groups in Organic Synthesis", Second Edition, John Wiley and Sons, New York, 1991; (b) displacement of a leaving group (halide, mesylate, tosylate, etc) with a primary or secondary amine, thiol or alcohol to form a secondary or tertiary amine, thioether or ether, respectively; (c) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; (d) reductive amination of a primary or secondary amine using an aldehyde.

The compounds of the present invention may have asymmetric carbon atoms. Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. Unless otherwise excluded, all such isomers, including diastereomeric mixtures and pure enantiomers are considered as part of the invention.

The compounds of the invention that are basic in nature are capable of forming a wide variety of different salts with various inorganic and organic acids. Although such salts must be pharmaceutically acceptable for administration to animals, it is often desirable in practice to initially isolate the compounds of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the invention. Such non-toxic base salts include those derived from such pharmacologically acceptable cations as sodium, potassium, calcium, and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention may be modulators of 11βHSD1. The compounds of the present invention may modulate processes mediated by 11βHSD1, which refer to biological, physiological, endocrinological, and other bodily processes which are mediated by receptor or receptor combinations which are responsive to the 11βHSD1 inhibitors described herein (e.g., diabetes, hyperlipidemia, obesity, impaired glucose tolerance, hypertension, fatty liver, diabetic complications (e.g. retinopathy, nephropathy, neurosis, cataracts and coronary artery diseases and the like), arteriosclerosis, pregnancy diabetes, polycystic ovary syndrome, cardiovascular diseases (e.g. ischemic heart disease and the like), cell injury (e.g.) brain injury induced by strokes and the like) induced by atherosclerosis or ischemic heart disease, gout, inflammatory diseases (e.g. arthrosteitis, pain, pyrexia, rheumatoid arthritis, inflammatory enteritis, acne, sunburn, psoriasis, eczema, allergosis, asthma, GI ulcer, cachexia, autoimmune diseases, pancreatitis and the like), cancer, osteoporosis and cataracts. Modulation of such processes can be accomplished in vitro or in vivo. In vivo modulation can be carried out in a wide range of subjects, such as, for example, humans, rodents, sheep, pigs, cows, and the like.

The compounds according to the present invention may be used in several indications which involve modulations of 11βHSD1 enzyme. Thus, the compounds according to the present invention may be used against dementia (See WO97/07789), osteoporosis (See Canalis E 1996, "Mechanisms of Glucocorticoid Action in Bone: Implications to Glucocorticoid-Induced Osteoporosis", Journal of Clinical Endocrinology and Metabolism, 81, 3441-3447) and may also be used disorders in the immune system (see Franchimont, et. al, "Inhibition of Th1 Immune Response by Glucocorticoids: Dexamethasone Selectively Inhibits IL-1 2-induced Stat 4 Phosphorylation in T Lymphocytes", *The Journal of Immunology* 2000, Feb. 15, vol 164 (4), pages 1768-74) and also in the above listed indications.

Inhibition of 11βHSD1 in isolated murine pancreatic , β-cells improves the glucose-stimulated insulin secretion (Davani, B., et al. (2000) *J. Biol. Chem*. Nov. 10, 2000; 275(45): 34841-4). Glucocorticoids were previously known to reduce pancreatic insulin release in vivo (Billaudel, B. and B. C. J. Sutter (1979) *Horm. Metab. Res.* 11: 555-560). Thus, inhibition of 11βHSD1 is predicted to yield other beneficial effects for diabetes treatment, besides effects on liver and fat.

Recent data suggests that the levels of the glucocorticoid target receptors and the 11βHSD1 enzymes determine the susceptibility to glaucoma (Stokes, J., et al., (2000) *Invest.* Ophthalmol. 41:1629-1638). Further, inhibition of 11βHSD1 was recently presented as a novel approach to lower the intraocular pressure (Walker E. A., et al, poster P3-698 at the Endocrine society meeting Jun. 12-15, 1999, San Diego). Ingestion of carbenoxolone, a non-specific inhibitor of 11βHSD1, was shown to reduce the intraocular pressure by 20% in normal subjects. In the eye, expression of 11βHSD1 is confined to basal cells of the corneal epithelium and the non-pigmented epithelialium of the cornea (the site of aqueous production), to ciliary muscle and to the sphincter and dilator muscles of the iris. In contrast, the distant isoenzyme 11 beta-hydroxysteroid dehydrogenase type 2 is highly expressed in the non-pigmented ciliary epithelium and corneal endothelium. None of the enzymes is found at the trabecular meshwork, the site of drainage. Thus, 11βHSD1 is suggested to have a role in aqueous production, rather than drainage, but it is presently unknown if this is by interfering with activation of the glucocorticoid or the mineralocorticoid receptor, or both.

Bile acids inhibit 11-β-hydroxysteroid dehydrogenase type 2. This results in a shift in the overall body balance in favor of cortisol over cortisone, as shown by studying the ratio of the urinary metabolites (Quattropani C, Vogt B, Odermatt A, Dick B, Frey B M, Frey F J. 2001. *J Clin Invest.* Nov; 108(9): 1299-305. "Reduced Activity of 11 -beta-hydroxysteroid dehydrogenase in Patients with Cholestasis"). Reducing the activity of 11βHSD1 in the liver by a selective inhibitor is predicted to reverse this imbalance, and acutely counter the symptoms such as hypertension, while awaiting surgical treatment removing the biliary obstruction.

The compounds of the present invention may also be useful in the treatment of other metabolic disorders associated with impaired glucose utilization and insulin resistance include major late-stage complications of NIDDM, such as diabetic angiopathy, atherosclerosis, diabetic nephropathy, diabetic neuropathy, and diabetic ocular complications such as retinopathy, cataract formation and glaucoma, and many other conditions linked to NIDDM, including dyslipidemia glucocorticoid induced insulin resistance, dyslipidemia, polycysitic ovarian syndrome, obesity, hyperglycemia, hyperlipidemia, hypercholesteremia, hypertriglyceridemia, hyperinsulinemia, and hypertension. Brief definitions of these conditions are available in any medical dictionary, for instance, *Stedman's Medical Dictionary* (10th Ed.).

INHIBITION OF 11βHSD1 ACTIVITY

11 βHSD1 Enzymatic Assay

The 11βHSD1 assay was performed in a 100 mM Triethanolamine buffer pH 8.0, containing 200 mM NaCl, 0.02% n-dodecyl β-D-maltoside, 5% glycerol, 5 mM β-mercaptoethanol. A typical reaction for the determination of $K_{iapp}$ values was carried at room temperature in a Corning® u-bottom 96-well plate and is described as follows: 11βHSD1 enzyme (5 nM, final concentration) was pre-incubated in the presence of the inhibitor and NADPH (500 μM, final concentration) for at least 30 minutes in the assay buffer. When pre-incubation was completed, the reaction was initiated by adding the regenerating system (2 mM Glucose-6-Phosphate, 1 U/mL Glucose-6-Phosphate dehydrogenase, and 6 mM MgCl$_2$, all the concentration reported are final in the assay buffer), and 3H-cortisone (200 nM, final concentration). After 60 minutes, 60 μL of the assay mixture was transferred to a second 96-well plate and mixed with an equal volume of dimethylsulfoxide to stop the reaction. A 15 μL aliquot from the reaction mixture was loaded into a C-18 column (Polaris C18-A, 50×4.6 mm, 5μ, 180 Angstrom from Varian) connected to an automated High-throughput Liquid Chromatography instrument developed by Cohesive Technologies, commercially available from Franklin, Mass. USA, with a β-RAM model 3 Radio-HPLC detector from IN/US, commercially available from Tampa, Fla. USA. The substrate and product peaks were separated by using an isocratic mixture of 43:57 methanol to water (v/v) at a flow rate of 1.0 mL/min.

The initial reaction velocities were measured by stopping the reaction at 60 min and by measuring the area of product formation in the absence and the presence of various concentrations of inhibitors. The $K_{iapp}$ values were determined using the equation for tight-binding inhibitor developed by Morrison, J F. (Morrison J F. Biochim Biophys Acta. 1969; 185: 269-86):

$$\frac{v_i}{v_o} = 1 - \left( \frac{(I + E + K_i) - \sqrt{(I + E + K_i)^2 - 4.I.E}}{2.I} \right)$$

Where $v_i$, and $v_o$ are the rates of cortisol formation in the presence and in the absence of inhibitor, respectively, I is the inhibitor concentration and E is the 11βHSD1 concentration in the assay buffer. All the concentrations reported are the final concentrations in the assay buffer See also Morrison, J. F., "Kinetics of the reversible inhibition of enzyme-catalysed reactions by tight-binding inhibitors," Biochim Biophys Acta., 1969; 185: 269-86.

The $K_{iapp}$ values of the compounds of the present invention for the 11βHSD1 enzyme may lie typically between about 10 nM and about 10 μM. The compounds of the present invention that were tested all have $K_{iapp}$'s in at least one of the above SPA assays of less than 1 μM, preferably less than 100 nM. Certain preferred groups of compounds possess differential selectivity toward the various 11-β-HSD's. One group of preferred compounds possesses selective activity towards 11βHSD1 over 11β-HSD-2. Another preferred group of compounds possesses selective activity towards 11βHSD-2 over 11 βHSD1. (Morrison J F. Biochim Biophys Acta. 1969; 185: 269-86).

Percentage of inhibition was determined in a 100 mM Triethanolamine buffer, pH 8.0, 200 mM NaCl, 0.02% n-dodecyl β-D-maltoside and 5mM β-ME. A typical reaction was carried on a Corning® u-bottom 96-well plate and is described as follows: 11βHSD1 enzyme (5 nM, final concentration) was pre-incubated in the presence of the inhibitor and NADPH (500 μM, final concentration) for at least 30 minutes in the assay buffer. When pre-incubation was completed, the reaction was initiated by adding the regenerating system (2 mM Glucose-6-Phosphate, 1 U/mL Glucose-6-Phosphate dehydrogenase, and 6 mM MgCl$_2$, all the concentration reported are final in the assay buffer), and 3H-cortisone (200 nM, final concentration). After 60 minutes, 60 μL of the assay mixture was transferred to a second 96-well plate and mixed with an equal volume of dimethylsulfoxide to stop the reaction. A 15 μL aliquot from the reaction mixture was loaded into a C-18 column (Polaris C18-A, 50×4.6 mm, 5μ, 180 Angstrom from Varian) connected to an automated High-throughput Liquid Chromatography instrument developed by Cohesive Technologies commercially available from Franklin, Mass., with a β-RAM model 3 Radio-HPLC detector from IN/US commercially available from Tampa, Fla. The substrate and product peaks were separated by using an isocratic mixture of 43:57 methanol to water (v/v) at a flow rate of 1.0 mL/min.

Percent Inhibition was calculated based on the following equation: (100−(3H-Cortisol peak area with inhibitor/3Hcortisol peak area without inhibitor)×100). Certain groups of compounds possess differential selectivity toward the various 11-β-HSD enzymes. One group of compounds possesses selective activity towards 11βHSD1 enzyme over 11 βHSD1-2 enzyme. While another group of compounds possesses selective activity towards 11 βHSD-2 enzymes over 11βHSD1 enzymes.

[1,2-3H]-cortisone is commercially available from American Radiolabeled Chemicals Inc. of St. Louis, Mo. USA. NADPH while Glucose-6-Phosphate and Glucose-6-Phosphate dehydrogenase was purchased from Sigma®.

HEK293-11 βHSD1/GRE-Luciferase Cell-Based Assay

Inhibition of 11βHSD1 enzyme activity was also measured using human kidney HEK293 stable transfected cells, over-expressing human 11βHSD1, and a reporter plasmid containing DNA sequences for specific recognition of glucocorticoid-activated glucocorticoid receptors (GRE), using a method similar to that described in Bujalska et al, Human 11β-hydroxysteroid dehydrogenase: Studies on the stably transfected isoforms and localization of the type 2 isozyme within renal tissue, Steroids, 62(1), 1991, 77-82 . These sequences were fused to a luciferase reporter gene (Luc) allowing for quantification of 11 βHSD1 enzyme modulation. 11βHSD1 is responsible for converting inactive into active glucocorticoids (cortisone to cortisol, in humans). Cortisol (but not cortisone) binds and activates glucocorticoid receptors (GR), which will result in activation of luciferase and production of light (assay readout). A compound with the capability of inhibiting 11βHSD1 will reduce the luciferase signal, as compared to the cortisone control (enzyme substrate).

Cells were plated in 384 Well Flat Bottom White Polystyrene TC-Treated Microplates, at 20,000 cell/well at a volume of 40 μl/well, in serum-free DME Medium. Plates were incubated at 37° C., 5% $CO_2$ overnight before addition of inhibitor compounds. Different concentrations of inhibitor compounds were added in 10% (v/v) dimethylsulfoxide (5 μL/well), followed by addition of 3 μM Cortisone (5 μL/well), and cells were incubated at 37° C. (5% $CO_2$) for six hours. At the end of the incubation, 25 μL/well SteadyLite HTS were added and plates were incubated 10min at room temp on shaker. Plates were then read on Top Count using 384HSD1 program. The concentration of inhibitor compound causing 50% inhibition of light signal was determined via a custom made Excel Macro. All results were compared to 100% activation control, i.e. cells treated only with cortisone (no inhibitors added).

Human Fa2N-4 Immortalized Cell-Based Assay

Fa2N4 is a cell line derived from human hepatocytes, developed by MultiCell Technologies, Inc. (U.S. Pat. No. 6,107,043), and commercialized by XenoTech LLC via an exclusive license. These cells are uniquely similar, both morphologically and functionally, to primary cultures, therefore exhibiting many of the characteristics of normal human hepatocytes, and thus providing a virtually limitless and reproducible supply of cells to support drug discovery. Inhibition of 11βHSD1 enzyme activity was assessed in this cell model by measuring decrease in cortisol (enzyme product) accumulation in cultures co-treated with cortisone (enzyme substrate) and the potential enzyme inhibitor. Cortisol signal was quantitatively determined in the supernatant of treated cells by means of the Correlate-Enzyme Immunoassay (EIA)™Cortisol kit (Assay Designs, Inc.).

Cells were plated in 96 Well Flat Bottom Collagen-coated Microplates, 20,000 cell/well, in 200 µl/well MFE™ (Multifunctional Enhancing—XenoTech, LLC) medium, containing antibiotics (penicillin-streptomycin) and supplemented with 10% of heat inactivated fetal bovine serum. Plates were incubated at 37° C., 5% $CO_2$ overnight. The following day, and before addition of cortisone and inhibitor compounds, medium was changed to Hepatocyte Basal Medium (HBM—Cambrex Bio ScienceWalkersVille, Inc) containing only antibiotics. Thirty-minute pre-incubation with various concentrations of inhibitor compounds (20 µL/well), was followed by addition of 5 µM Cortisone (20 µL/well), and cells were incubated at 37° C., 5% $CO_2$ overnight. At the end of the incubation, 100 µL of each supernatant was analyzed for cortisol content using the Cortisol-EIA kit from Assay Designs, following manufacturers' instructions. Plates were read on a plate reader (Spectra MAX PLUS—Molecular Devices Corporation) at 405 nm, with correction at 580 nm. All results were compared to 100% activation control, i.e. cells treated only with cortisone (no inhibitors added).

Pharmaceutical Compositions/Formulations, Dosaging and Modes of Administration

Pharmaceutically acceptable salts of the claimed compounds include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of the claimed compounds may be prepared by one or more of three methods:

(i) by reacting the claimed compounds with the desired acid or base;

(ii) by removing an acid- or base-labile protecting group from a suitable precursor of the claimed compounds or by ring-opening a suitable cyclic precursor, for example, a lactone or lactam, using the desired acid or base; or (iii) by converting one salt of the claimed compounds to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in *Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see *Chem Commun*, 17, 1889-1896, by O. Almarsson and M. J. Zaworotko (2004). For a general review of multi-component complexes, see *J Pharm Sci*, 64 (8),1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to the claimed compounds include references to salts, solvates, multi-component complexes and liquid crystals thereof and to solvates, multi-component complexes and liquid crystals of salts thereof.

The compounds of the invention include the claimed compounds as hereinbefore defined, including all polymorphs and crystal habits thereof, prodrugs and isomers thereof (including optical, geometric and tautomeric isomers) as hereinafter defined and isotopically-labeled claimed compounds.

As indicated, so-called 'prodrugs' of the claimed compounds are also within the scope of the invention. Thus certain derivatives of the claimed compounds which may have little or no pharmacological activity themselves can, when administered into or onto the body, be converted into the claimed compounds having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the claimed compounds with certain moieties known to those skilled in the art as 'pro-moieties' as described, for example, in *Design of Prodrugs* by H. Bundgaard (Elsevier, 1985).

Some examples of prodrugs in accordance with the invention include (i) where the claimed compounds contains a carboxylic acid functionality (—COOH), an ester thereof, for example, a compound wherein the hydrogen of the carboxylic acid functionality of the claimed compounds is replaced by (C$_1$-C$_8$) alkyl;

(ii) where the compound of the claimed compounds contains an alcohol functionality (—OH), an ether thereof, for example, a compound wherein the hydrogen of the alcohol functionality of the claimed compounds is replaced by (C$_1$-C$_6$)alkanoyloxymethyl; and (iii) where the claimed compounds contains a primary or secondary amino functionality (—NH$_2$ or —NHR where R≠H), an amide thereof, for example, a compound wherein, as the case may be, one or both hydrogens of the amino functionality of the claimed compounds is/are replaced by (C$_1$-C$_{10}$)alkanoyl.

Further examples of replacement groups in accordance with the foregoing examples and examples of other prodrug types may be found in the aforementioned references.

Moreover, certain claimed compounds may themselves act as prodrugs of other claimed compounds. Also included within the scope of the invention are metabolites of compounds of the claimed compounds, that is, compounds formed in vivo upon administration of the drug. Some examples of metabolites in accordance with the invention include (i) where the claimed compounds contains a methyl group, an hydroxymethyl derivative thereof (—CH$_3$->—CH$_2$OH):

(ii) where the compound of the claimed compounds contains an alkoxy group, an hydroxy derivative thereof (—OR ->—OH);

(iii) where the claimed compounds contain a tertiary amino group, a secondary amino derivative thereof (—NR$^1$R$^2$->—NHR$^1$ or —NHR$^2$);

(iv) where the claimed compounds contain a secondary amino group, a primary derivative thereof (—NHR$^1$->—NH$_2$);

(v) where the claimed compounds contain a phenyl moiety, a phenol derivative thereof (—Ph->—PhOH); and (vi) where the claimed compounds contain an amide group, a carboxylic acid derivative thereof (—CONH$_2$->COOH).

The claimed compounds containing one or more asymmetric carbon atoms can exist as two or more stereoisomers. Where the claimed compounds contain an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in the claimed containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the claimed compounds, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC).

Alternatively, the racemate (or a racemic precursor) may be reacted with a suitable optically active compound, for example, an alcohol, or, in the case where the claimed compounds contain an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled claimed compounds wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled claimed compounds, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled claimed compounds can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of the claimed compounds as hereinbefore defined, all salts, solvates and complexes thereof and all solvates and complexes of salts thereof as defined hereinbefore for compounds of the claimed compounds. The invention includes all polymorphs of the aforementioned species and crystal habits thereof.

When preparing the claimed compounds in accordance with the invention, it is open to a person skilled in the art to routinely select the form of compound that provides the best combination of features for this purpose. Such features include the melting point, solubility, processability and yield of the intermediate form and the resulting ease with which the product may be purified on isolation.

Drug Product

The claimed compounds should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Examples of pharmaceutically active agents useful in combination may include anti-infectives, including, without limitation, antibiotics, antivirals, and antifungals; antiallergenic agents and mast cell stabilizers; steroidal and non-steroidal anti-inflammatory agents (such as nepafenac); cyclooxygenase inhibitors, including, without limitation, Cox I and Cox II inhibitors; combinations of anti-infective and anti-inflammatory agents; decongestants; anti-glaucoma agents, including, without limitation, adrenergics, beta-adrenergic blocking agents, alpha-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of age related macular degeneration (AMD) including nonexudative (dry AMD) and exudative (wet AMD), including, without limitation, angiogenesis inhibitors, including angiogenesis inhibitors that inhibit protein kinase receptors, including protein kinase receptors that are VEGF receptors; and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of posterior segment 26, including, without limitation, age related macular degeneration including nonexudative (dry AMD) and exudative (wet AMD), choroidal neovascularization, retinopathies, retinitis, uveitis, macular edema, and glaucoma. Such angiostatic steroids are more fully disclosed in U.S. Pat. Nos. 5,679,666 and 5,770,592. A non-steroidal anti-inflammatory for the treatment of cystoid macular edema is nepafenac.

Generally, the pharmaceutical compositions of the invention will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in *Expert Opinion in Therapeutic Patents*, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise the claimed compounds, a film-forming polymer, a binder, a solvent, a humectant, a plasticiser, a stabiliser or emulsifier, a viscosity-modifying agent and a solvent. Some components of the formulation may perform more than one function.

The claimed compounds may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the claimed compounds may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864, herein incorporated by reference in its entirety. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of the claimed compounds used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci*, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insulator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise the claimed compounds, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

Rectal/Intravacinal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

For administration to the eye, a compound of the present invention is delivered in a pharmaceutically acceptable ophthalmic vehicle such that the compound is maintained in contact with the ocular surface for a sufficient time period to allow the compound to penetrate the cornea and/or sclera and internal regions of the eye, including, for example; the anterior chamber, posterior chamber, vitreous body, aqueous humor, vitreous humor, cornea, iris/cilary, lens, choroid/retina and sclera. The pharmaceutically acceptable ophthalmic vehicle may be an ointment, vegetable oil, or an encapsulating material. A compound of the invention may also be injected directly into the vitreous humor or aqueous humor.

Further, a compound may be also be administered by well-known, acceptable methods, such as subtebnon and/or subconjunctival injections. For treatment of AMD, CNV, retinopathies, retinitis, uveitis, cystoid macular edema (CME), glaucoma, and other diseases or conditions of the posterior segment of the eye, it is preferable to dispose a depot of a specific quantity of an ophthalmically acceptable pharmaceutically active agent directly on the outer surface of the sclera and below Tenon's capsule. In addition, in cases of AMD and CME it is most preferable to dispose the depot directly on the outer surface of the sclera, below Tenon's capsule, and generally above the macula.

In addition to the formulations described above, the compounds may also be formulated as a depot preparation. Such long-acting formulations may be administered by implantation (for example, subcutaneously or intramuscularly) intramuscular injection or by the above mentioned subtenon or intravitreal injection.

Within particular embodiments of the invention, the compounds may be prepared for topical administration in saline (combined with any of the preservatives and antimicrobial agents commonly used in ocular preparations), and administered in eyedrop form. The solution or suspension may be prepared in its pure form and administered several times daily. Alternatively, present compositions, prepared as described above, may also be administered directly to the cornea.

Alternatively, the active ingredient may be in powder form for constitution with a suitable vehicle, e.g., sterile pyrogen-free water, before use.

Within further alternative embodiments, the composition is prepared with a muco-adhesive polymer which binds to cornea. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

Within further embodiments, the present compositions may be utilized as an adjunct to conventional steroid therapy.

Pharmaceutical carriers for hydrophobic components may also be employed. A pharmaceutical carrier for hydrophobic compounds is a cosolvent system comprising benzyl alcohol, a nonpolar surfactant, a water-miscible organic polymer, and an aqueous phase. The cosolvent system may be a VPD cosolvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. The proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-Of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains the claimed compounds in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 0.5 mg/kg body wieght to about 100 mg/kg depending, of course, on the mode of administration. The preferred dosage rate is between 30 mg/kg body weight to about 100 mg/kg body weight. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

EXAMPLES

The examples, methods, and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The structures of the compounds are confirmed by either elemental analysis or NMR, where peaks assigned to the characteristic protons in the titled compound are presented where appropriate. $^1$H NMR shift ($\delta_H$) are given in parts per million (ppm) down filed from an internal reference standard.

The invention will now be described in reference to the following EXAMPLES. These EXAMPLES are not to be regarded as limiting the scope of the present invention, but shall only serve in an illustrative manner.

METHOD A

Example 1

N-(6-amino-4-methylpyridin-2-yl)-2-(4-cyanophenyl)-4-methyl-1,3-thiazole-5-sulfonamide

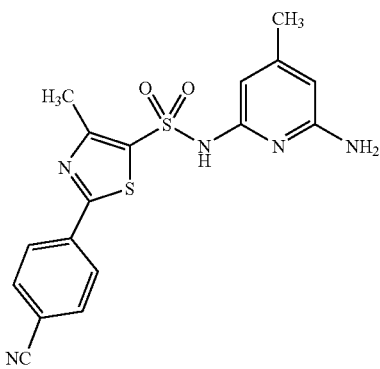

i. Preparation of tert-Butyl (6-amino-4-methylpyridin-2-yl)carbamate

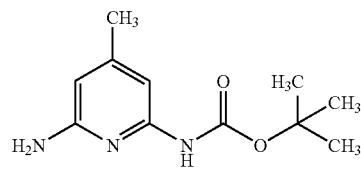

To a solution of 4-methyl-pyridin-2,6-diamine (2.13 g, 17.3 mmol, 1 equiv) in tetrahydrofuran (18 mL) at 0° C. was added lithium bis(trimethylsilyl)amide (34.6 mL, 1 M). After 30 min, di-tert-butyl dicarbonate (3.78 g, 17.3 mmol) was added to the reaction mixture. Upon completion, the reaction was warmed to 24° C. and concentrated in vacuo (~25 mm Hg). A 1:1 solution of saturated aqueous ammonium chloride and brine (100 mL) was added to the resulting solid. The resulting mixture was extracted with ethyl acetate (3×100 mL). Purification by high performance flash chromatography (0→30% ethyl acetate in hexanes) provided the carbamate intermediate (1.94 g, 50%). $^1$H NMR (CDCl$_3$, 400 MHz), δ: 7.12 (s, 1H), 7.09 (br s, 1H), 6.02 (br s, 2H), 2.23 (s, 3H), 1.51 (s, 9H); LRMS (ESI) m/z: 224.2.

ii. Preparation of tert-Butyl [6-({[2-(acetylamino)-4-methyl-1,3-thiazol-5-yl]sulfonyl}amino)-4-methylpyridin-2-yl]carbamate

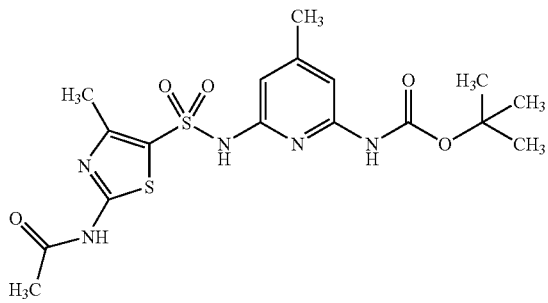

To a solution of tert-butyl (6-amino-4-methylpyridin-2-yl)carbamate (1.2 g, 6.0 mmol) in pyridine (30 mL) was added 2-acetamido-4-methyl-5-thiazolesulfonyl chloride (1.5 g, 6.0 mmol). The resulting mixture was stirred at 24° C. for 16 hours. The reaction was concentrated in vacuo (~25 mm Hg). Purification by high performance flash chromatography (0→5% methanol in dichloromethane) provided the intermediate (2.1 g, 80%). $^1$H NMR (400 MHz, CDCl$_3$), δ: 7.43 (br s, 1H), 6.99 (s, 1H), 5.31 (s, 1H) 2.34 (s, 3H), 2.31 (s, 3H), 2.22 (s, 3H), 1.54 (s, 9H); LRMS (ESI) m/z: 342 [M-CO$_2$C(CH$_3$)$_3$]$^+$.

iii. Preparation of tert-Butyl (6-{[(2-amino-4-methyl-1,3-thiazol-5-yl)sulfonyl]amino}-4-methylpyridin-2-yl)carbamate

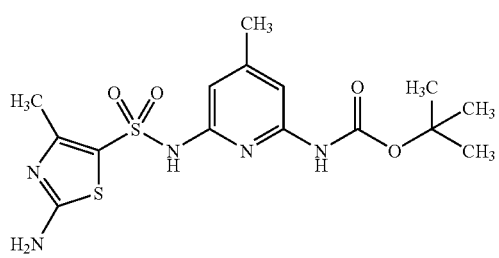

A solution of tert-butyl [6-({[2-(acetylamino)-4-methyl-1,3-thiazol-5-yl]sulfonyl}amino)-4-methylpyridin-2-yl]carbamate (2.1 g, 4.8 mmol, 1 equiv) and 1 N aqueous sodium hydroxide (7.2 mL) in methanol (30 mL) was heated to 50° C. for 48 h. Upon cooling to 24° C., the reaction mixture was concentrated in vacuo (~25 mm Hg). The resulting solid was dissolved in water (20 mL). The solution was neutralized with concentrated hydrochloric acid until pH=7. The resulting solid was collected by filtration, washed with water (30 mL) and diethyl ether (2×30 mL) (1.59 g, 83%). $^1$H NMR (400 MHz, CDCl$_3$), δ: 8.29 (br s, 1H), 7.48 (s, 1H), 6.91 (s, 1H), 2.40 (s, 3H), 2.33 (s, 3H), 1.52 (s, 9H); LCMS (ESI) m/z: 400.2.

iv. Preparation of tert-Butyl (6-{[(2-bromo-4-methyl-1,3-thiazol-5-yl)sulfonyl]amino}-4-methylpyridin-2-yl)carbamate

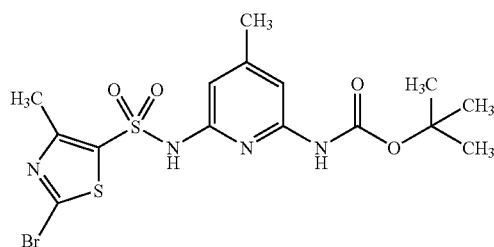

To a suspension of tert-butyl (6-{[(2-amino-4-methyl-1,3-thiazol-5-yl)sulfonyl]amino}-4-methylpyridin-2-yl)carbamate (1.59 g, 3.98 mmol, 1 equiv) and copper (II) bromide (0.55 g, 2.47 mmol, 0.62 equiv) in acetonitrile (30 mL) at 65° C. was added tert-butyl nitrite (0.71 mL, 5.97 mmol, 1.5 equiv). The reaction mixture turned from green to red and gas evolution was observed. After 10 minutes when gas evolution ceased, the reaction mixture was cooled to 24° C. and concentrated in vacuo (~25 mm Hg). The resulting solid was dissolved in ethyl acetate (30 mL), and the resulting solution was washed with water (30 mL) that had been acidified with sulfuric acid (0.5 mL). The collected organic was dried over v. Preparation of tert-Butyl [6-({[2-(4-cyanophenyl)-4-methyl-1,3-thiazol-5-yl]sulfonyl}-amino)-4-methylpyridin-2-yl]carbamate

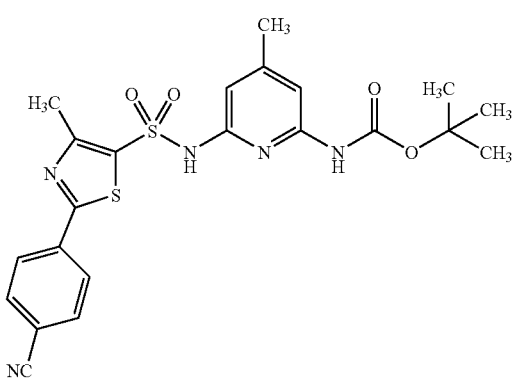

A solution of tert-butyl (6-{[(2-bromo-4-methyl-1,3-thiazol-5-yl)sulfonyl]amino}-4-methylpyridin-2-yl)carbamate (0.96 g, 2.08 mmol, 1 equiv), 4-cyanophenylboronic acid (0.336 g, 2.29 mmol, 1.1 equiv), and cesium carbonate (2.03 g, 6.24 mmol, 3 equiv) in 2:1 dimethoxyethane/water (30 mL) was purged with nitrogen for 15 minutes. Dichloro[1,1'-bis(diphenylphosphine)ferrocene] palladium (II) chloride (0.068 g, 0.08 mmol, 0.04 equiv) was then added, and the resulting mixture was purged with nitrogen for another 15 minutes. The reaction was heated to 80° C. for 1 h. After cooling to 24° C., the solution was concentrated in vacuo (~25 mm Hg). The resulting aqueous mixture was extracted ethyl acetate (60 mL). The collected organic was dried over anhydrous sodium sulfate, filtered, and concentrated. Purification by high performance flash chromatography (0→10% ethyl acetate in hexanes) provided the intermediate (0.334 g, 33%). $^1$H NMR (400 MHz, CDCl$_3$), δ: 7.97 (d, J=8.3 Hz, 2H), 7.73 (d, J=8.3 Hz, 2H), 7.63 (br s, 1H), 7.43 (s, 1H), 6.90 (s, 1H), 2.65 (s, 3H), 2.32 (s, 3H), 1.50 (s, 9H); LRMS (ESI) m/z: 486.1.

vi. Preparation of N-(6-Amino-4-methylpyridin-2-yl)-2-(4-cyanophenyl)4-methyl-1,3-thiazole-5-sulfonamide To a solution of tert-butyl [6-({[2-(4-cyanophenyl)4-methyl-1,3-thiazol-5-yl]sulfonyl}amino)-4-methylpyridin-2-yl]carbamate (0.334 g, 0.68 mmol, 1 equiv) in dichloromethane (3 mL) was added trifluoroacetic acid (0.21 mL, 4 equiv). The reaction mixture was stirred at 24° C. for 48 h. The solution was neutralized with saturated aqueous sodium bicarbonate, and the resulting solution was extracted with dichloromethane (3×20 mL). The collected organic was dried over anhydrous sodium sulfate, filtered, and concentrated. Purification by high performance flash chromatography (0→1% methanol in dichloromethane) provided the titled product N-(6-Amino-4-methylpyridin-2-yl)-2-(4-cyanophenyl)-4-methyl-1,3-thiazole-5-sulfonamide (0.22 g, 81%). $^1$H NMR (400 MHz, DMSO-d$_6$), δ: 12.08 (br s, 1H), 8.09 (d, J=8.3 Hz, 2H), 7.95 (d, J=8.3 Hz, 2H), 6.62 (br s, 2H), 6.12 (s, 1H), 5.79 (s, 1H), 2.59 (s, 3H), 2.08 (s, 3H); HRMS (ESI): Calculated for C$_{17}$H$_{16}$N$_5$O$_2$S$_2$ m/z 386.0740. Found: 386.0745;. Anal. Calcd for C$_{17}$H$_{15}$N$_5$O$_2$S$_2$: C, 52.97; H, 3.92; N, 18.17; Found: C, 52.75; H, 3.76; N, 18.03.

METHOD B

Example 2

(+)-4'-Cyano-N-[6-(1-hydroxvethyl)pyridin-2-yl]biphenyl4-sulfonamide and (−)-4'-Cyano -N-[6-(1-hydroxyethyl)pyridin-2-yl]biphenyl-4-sulfonamide

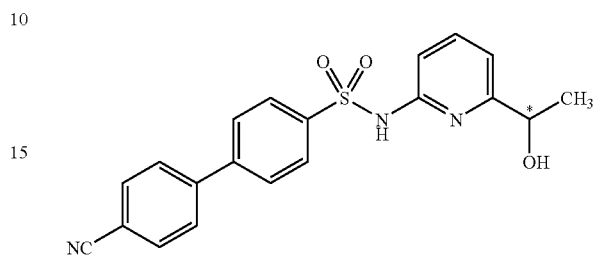

i. Preparation of N-[6-(1-Hydroxyethyl)pyridin-2-yl]-2,2-dimethylpropanamide

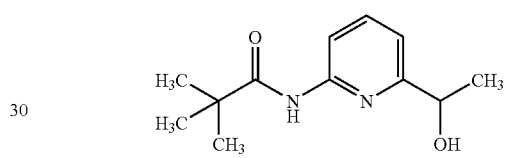

To an ice-cooled solution of N-(6-formylpyridin-2-yl)-2,2-dimethylpropanamide (4.0 g, 19.4 mmol) in tetrahydrofuran (30 mL) was added methylmagnesium chloride (13.6 mL, 40.7 mmol, 3 M in THF) dropwise. After 2 h the reaction was quenched with saturated aqueous NH$_4$Cl solution (10 mL) and diluted with ethyl acetate (50 mL). The mixture was washed with saturated aqueous NaHCO$_3$ solution (2×50 mL). The organic layer was dried over anhydrous Na$_2$SO$_4$, filtered, and concentrated. The resulting residue was purified by flash column chromatography (2:1 hexanes/EtOAc) to afford the intermediate as a clear oil (0.56 g, 49%). $^1$H NMR (400 MHz, CDCl$_3$), δ: 8.14 (d, J=8.1 Hz, 1H), 8.00 (br s, 1H), 7.70 (t, J=7.8 Hz, 1H), 7.00 (d, J=7.5 Hz, 1H), 4.82 (m, 1H), 3.81 (d, J=5.0 Hz, 1H), 1.49 (d, J=6.5 Hz, 3H), 1.35 (s, 9H); LRMS (ESI): m/z: 223.2.

ii. Preparation of 1-(6-Aminopyridin-2-yl)ethanol

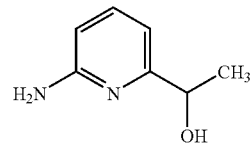

To a solution of N-[6-(1-hydroxyethyl)pyridin-2-yl]-2,2-dimethylpropanamide (2.0 g, 9.6 mmol) in dioxane (20 mL) was added 9 N aqueous HCl (10 mL). The reaction mixture was warmed to 100° C. for 24 h. After cooling to 25° C., the solution was neutralized with solid NaOH until pH=9 and diluted with EtOAc (50 mL). The resulting mixture was washed with saturated aqeuous NaHCO$_3$(2×30 mL). The organic layer was dried over anhydrous Na$_2$SO$_4$, filtered, and concentrated. The resulting residue was dissolved in dichloromethane (10:1, 5 mL). Diethyl ether (10 mL) was added, and the solution was allowed to stand for 24 h. The resulting crystals were filtered and rinsed with diethyl ether (2×10 mL) to afford the above-titled intermediate as a white solid (0.65 g, 49%). $^1$H NMR (400 MHz, CDCl$_3$), δ: 7.43 (t, J=7.5 Hz, 1H), 6.59 (d, J=7.3 Hz, 1H), 6.39 (d, J=8.1 Hz, 1H), 4.72 (q, J=6.3 Hz, 1H), 4.43 (bs, 2H), 4.21 (bs, 1H), 1.45 (d, J=6.3 Hz, 3H); LRMS (ESI): m/z: 139.1.

iii. (+)-4'-Cyano-N-[6-(1-hydroxyethyl)pyridin-2-yl]biphenyl4-sulfonamide and (−)4'-Cyano-N-[6-(1-hydroxyethyl)pyridin-2-yl]biphenyl4-sulfonamide To a solution of 1-(6-aminopyridin-2-yl)ethanol (0.20 g, 1.4 mmol) and diisopropylethyl amine (0.22 mL, 1.8 mmol) in dichloromethane (5 mL) was added chloro(trimethyl)silane (0.48 mL, 2.9 mmol). After 1 h, the reaction mixture was concentrated, and the resulting residue was dissolved in dichloromethane (2 mL) and pyridine (2 mL). 4'-Cyanobiphenyl-4-sulfonyl chloride (0.43 g, 1.53 mmol) was then added to the reaction mixture. After 3 h, the reaction mixture was concentrated in vacuo. The resulting residue was diluted with acetic acid (1 mL) and methanol (1 mL) and stirred for 0.5 h. The reaction mixture was then diluted with ethyl acetate (50 mL) and washed with saturated aqueous NaHCO$_3$ solution (2×30 mL). The organic layer was concentrated, and the resulting residue was purified by flash column chromatography (1:1 hexanes/ethyl acetate). The racemic product was converted to the hydrochloride salt by dissolving in diethyl ether (5 mL) and adding HCl (1 N in Et$_2$O) to afford the titled racemic product as a white solid (0.21 g, 37%). $^1$H NMR (400 MHz, CD$_3$OD), δ: 8.01 (d, J=8.3, 2H), 7.96 (t, J=8.1, 1H), 7.81 (d, J=8.6 Hz, 2H), 7.78-7.73 (m, 4H), 7.21-7.16 (m, 2H), 4.86 (q, J=6.6 Hz, 1H), 1.38 (d, J=6.6 Hz, 3H). HRMS (ESI): Calcd for C$_{20}$H$_{18}$N$_3$O$_3$S m/z: 380.1069; Found: 380.1061. Anal. Calcd for C$_{20}$H$_{17}$N$_3$O$_3$S. HCl: C, 57.76; H, 4.36; N, 10.10; Found: C, 57.87; H, 4.58; N, 9.88.

The racemic free base was separated by a preparative enantioseparation method which was developed using supercritical fluid chromatography (SFC) technology, with supercritical carbon dioxide providing the bulk of the mobile phase. The separation and isolation of chiral enantiomers was carried out on a Berger SFC MultiGram™ Purification System (Mettler Toledo AutoChem, Inc.). The preparative chromatography conditions used to separate the enantiomers consisted of a Chiralpak AD-H (amylose tris-(3,5-dimethylphenylcarbamate)) 250×21 mm, 5 µsemi-preparative column as the chiral stationary phase (Chiral Technologies, Inc.). Column temperature was maintained at 35° C. The mobile phase used was supercritical CO$_2$ with 40% methanol as the modifier, maintained isocratically at a flow rate of 50 mL/min and a constant pressure of 100 bar.

Enantiomer 1 [α]$_D$ (MeOH)=−66.67°.
Enantiomer 2 [α]$_D$ (MeOH)=+100°.

Example 3

(−)4'-cyano-N-[6-(1-hydroxypropyl)pyridin-2-yl]biphenyl4-sulfonamide and (+)-4'-cyano -N-[6-(1-hydroxypropyl)pyridin-2-yl]biphenyl-4-sulfonamide

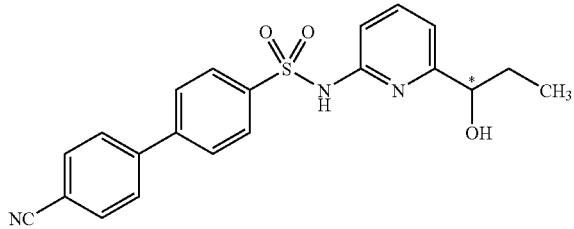

The above-titled racemic mixture was made using the procedures described above for the preparation of Example 2 above, except using ethylmagnesium bromide instead of methylmagnesium chloride. The racemic mixture was maintained as a free base without conversion to a salt. Purification by high performance flash chromatography (15→60% EtOAc in hexanes) gave the product (0.267 g, 83%) $^1$H NMR (400 MHz, CDCl$_3$), δ: 8.05 (d, J=8.3 Hz, 2H), 7.76 (m, 2H), 7.58-7.71 (m, 6H), 7.15 (d, J=8.3 Hz, 1H), 6.81 (d, J=7.6 Hz, 1H), 4.62 (dd, J=7.2, 4.9 Hz, 1H), 1.60-1.87 (m, 2H), 0.89(t, J=7.5 Hz, 3H); LRMS (ESI): m/z: 394.0.

The preparative enantioseparation method was similar to that used for Example 2 above. The preparative chromatography conditions used to separate the enantiomers consisted of a Chiralpak AD-H (amylose tris-(3,5-dimethylphenylcarbamate)) 250×21 mm, 5 µsemi-preparative column as the chiral stationary phase (Chiral Technologies, Inc.). Column temperature was maintained at 35° C. The mobile phase used was supercritical CO$_2$ with 45% methanol as the modifier, maintained isocratically at a flow rate of 55 mL/min and a constant pressure of 140 bar. Sample was solubilized in methanol to 100 mg/mL, and a column loadability of 50 mg per 1 mL injection was attained. The total run time for each injection was 6.1 minutes. The retention times for the first enantiomer (−) was 4.0 minutes, while the 2$^{nd}$ eluting enantiomer (+) eluted from the column at 5.0 minutes. The specific optical rotations, [α]$_D$, for (−) and (+) were determined to be −17.34° and +22.29°, respectively.

Enantiomer 1: (−)4'-cyano-N-[6-(1-hydroxypropyl)pyridin-2-yl]biphenyl-4-sulfonamide. [α]$_D$ (MeOH)=−17.34°; Anal. Calcd for C$_{21}$H$_{19}$N$_3$O$_5$S.0.17 H$_2$O: C, 63.61; H, 4.92; N, 10.60. Found: C, 63.59; H, 4.93; N, 10.60.

Enantiomer 2: (+)-4'-cyano-N-[6-(1-hydroxypropyl)pyridin-2-yl]biphenyl-4-sulfonamide. [α]$_D$ (MeOH)=+22.29°; Anal. Calcd for C$_{21}$H$_{19}$N$_3$O$_5$S.0.14 H$_2$O: C, 63.70; H, 4.91; N, 10.61. Found: C, 63.68; H, 4.92; N, 10.45.

Example 4

(+)-4'-Cyano-N-[6-(1-hydroxyethyl)pyridin-2-yl]-3-methylbiphenyl-4-sulfon-amide and (−)-4'-Cyano-N-[6-(1-hydroxyethyl)pyridin-2-yl]-3-methylbiphenyl-4-sulfon-amide

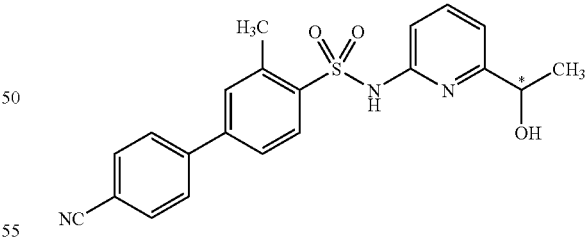

The reagent 4-Bromo-2-methyl-N-(6-{1-[(trimethylsilyl)oxy]ethyl}pyridin-2-yl)benzenesulfonamide was made following the procedure described for the preparation of 4'-Cyano-N-[6-(1-hydroxyethyl)pyridin-2-yl]biphenyl-4-sulfonamide in Example 2 above. To this sulfonamide reagent (0.11 g, 0.3 mmol) was added 4-cyanophenylboronic acid (0.087 g, 0.59 mmol), Pd(PPh$_3$)$_4$ (0.034, 0.03 mmol), sodium carbonate (0.1 g, 1.18 mmol), DMF (2 mL) and water (1 mL), and the mixture placed in a microwave tube and heated in a microwave at 200° C. for 30 minutes. The mixture was diluted with ethyl acetate and washed with saturated aqueous sodium bicarbonate, water and brine. The organic layer was dried over anhydrous sodium sulfate. Purification by high performance flash chromatography (15→70% EtOAc in hexanes) gave the above-titled product (0.081 g, 74%). $^1$H NMR (400 MHz, CDCl$_3$), δ: 8.19 (d, J=8.1 Hz, 1H), 7.70-7.77 (m, 2H), 7.63-7.69 (m, 2H), 7.57 (t, J=8.0 Hz, 1H), 7.46-7.53 m, 2H), 7.00 (m, 1H), 6.81 (m, 1H), 4.78 (m, 1H), 2.78 (s, 3H), 1.44 (d, J=6.6 Hz, 3H); HRMS (ESI) m/z calcd for C$_{21}$H$_{20}$N$_3$O$_5$S 394.1220, found 394.1215.

The preparative enantioseparation method was similar to that used for Example 2 above. The preparative chromatography conditions used to separate the enantiomers consisted of a Chiralcel OJ-H (cellulose tris-(4-methylbenzoate), 250× 21 mm, 5 μ semi-preparative column as the chiral stationary phase (Chiral Technologies, Inc.). Column temperature was maintained at 35° C. The mobile phase used was supercritical CO$_2$ with 25% isopropanol as the modifier, maintained isocratically at a flow rate of 50 mL/min and a constant pressure of 140 bar.

Enantiomer 1: (−)4'-Cyano-N-[6-(1-hydroxyethyl)pyridin-2-yl]-3-methylbiphenyl4-sulfonamide. [α]$_D$ (MeOH)=− 12.12°; Anal. Calcd for C$_{21}$H$_{19}$N$_3$O$_5$S.0.21 H$_2$O: C, 63.49; H, 4.93; N, 10.58. Found: C, 63.45; H, 4.73; N, 10.54.

Enantiomer 1: (+)4'-Cyano-N-[6-(1-hydroxyethyl)pyridin-2-yl]-3-methylbiphenyl4-sulfonamide. [α]$_D$ (MeOH)=+ 11.43°; Anal. Calcd for C$_{21}$H$_{19}$N$_3$O$_5$S.0.20 H$_2$O: C, 63.49; H, 4.92; N, 10.58. Found: C, 63.55; H, 4.85; N, 10.51.

Example 5

N-(6-aminopyridin-2-yl)-4-chloro-2-fluoro-5-methylbenzenesulfonamide

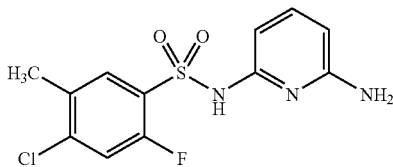

To a solution of 2,6-diaminopyridine (178 mg, 1.6 mmol, 2.2 equiv) in pyridine (7 mL) at 24° C. was added 4-chloro-2-fluoro-5-methylbenzenesulfonyl chloride (188 mg, 0.735 mmol, 1 equiv). After 18 h, the reaction mixture was concentrated in vacuo. The resulting residue was partitioned between saturated aqueous ammonium chloride solution (20 mL) and ethyl acetate (20 mL). The organic was separated, and the aqueous layer was extracted with ethyl acetate (2×20 mL). The collected organic was dried over anhydrous sodium sulfate, filtered, and concentrated. Purification by preparative HPLC provided the product (69 mg, 27%). $^1$H NMR (400 MHz, CDCl$_3$), δ: 7.80 (d, J=7.6 Hz, 1H), 7.42 (t, J=8.3 Hz, 1H), 7.08 (d, J=9.4 Hz, 1H), 6.83 (d, J=8.3 Hz, 1H), 6.00 (d, J=8.3 Hz, 1H),5.91(s, 2H), 2.38 (s, 3H); Calculated for C$_{12}$H$_{12}$N$_3$O$_2$ClFS m/z 316.0318. Found: 316.0322; Anal. Calcd for C$_{12}$H$_{11}$N$_3$O$_2$ClFS.0.27 CH$_3$CO$_2$H: C, 45.37; H, 3.67; N, 12.66; Found: C, 45.08; H, 3.67; N, 12.65.

Example 9

4'-cyano-N-[6-(hydroxymethyl)pyridin-2-yl]biphenyl-4-sulfonamide

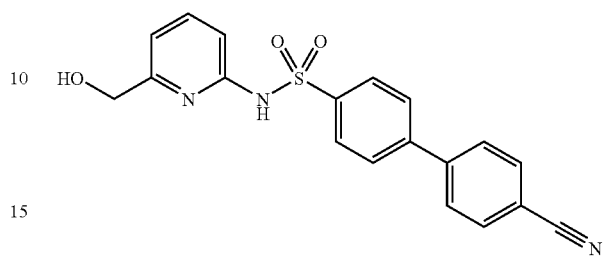

i. Preparation of N-[6-(1-Hydroxyethyl)pyridin-2-yl]-2,2-dimethylpropanamide

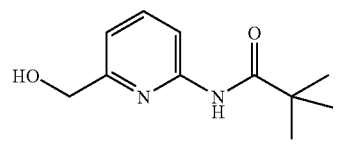

To solution of N-(6-formylpyridin-2-yl)-2,2-dimethylpropanamide (3.0 g, 14.9 mmol) in methanol (10 mL) was added sodium borohydride (1.37 g, 37.1 mmol) and stirred for 3 hours. The mixture diluted with ethyl acetate (50 mL). The mixture was washed with aqueous hydrochloric acid (2×30 mL, 0.1 N) and saturated sodium bicarbonate (2×50 mL). The organic layer was dried over anhydrous Na$_2$SO$_4$, filtered, and concentrated to afford the above-titled intermediate as a white solid (2.49 g, 80%). $^1$H NMR (400 MHz, CDCl$_3$), δ: 8.16 (d, J=8.3 Hz, 1H), 8.00 (br s, 1H), 7.71 (t, J=7.8 Hz, 1H), 7.12 (d, J=7.5 Hz, 1H), 4.05-3.96 (m, 2H), 1.35 (s, 9H); LRMS (ESI): m/z: 209.2.

ii. Preparation of (6-aminopyridin-2-yl)methanol

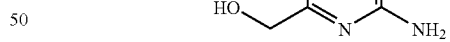

To a solution of dioxane (15 mL) was added N-[6-(1-hydroxyethyl)pyridin-2-yl]-2,2-dimethylpropanamide (1.5 g, 7.2 mmol) and aqueous hydrochloric acid (6N, 15 mL) and the mixture was stirred at 90° C. for 14 h. The solution was cooled 0° C., triturated with diethyl ether (2×30 mL) and the aqueous layer was neutralized using sodium hydroxide to approximately pH 8. The mixture was diluted with chloroform/IPA (10:1, 50 mL). The mixture was washed with saturated brine solution (2×50 mL). The organic layer was dried over anhydrous Na$_2$SO$_4$, filtered, and concentrated to afford the above-titled intermediate as a white solid (0.86 g, 96%). HPLC: R$_t$ 0.628 min. (99.5% area). $^1$H NMR (400 MHz, CDCl$_3$), δ: 7.48 (t, J=7.4 Hz, 1H), 6.66 (d, J=7.3 Hz, 1H), 6.50 (d, J=8.4 Hz, 1H), 4.58 (s, 2H), 4.23 (bs, 2H). LCMS (ESI): m/z: 125.2.

iii. Preparation of 6-({[tert-butyl(dimethyl)silyl]oxy}methyl)pyridin-2-amine

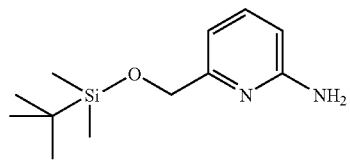

To a solution of dichloromethane (15 mL) was added (6-aminopyridin-2-yl)methanol (0.72 g, 5.8 mmol), tert-butyl(chloro)dimethylsilane (1.05 g, 6.95 mmol) and triethylamine (1.05 mL, 7.53 mmol). The mixture was stirred for 24 h and washed with saturated sodium bicarbonate (2×30 mL) and aqueous hydrochloric acid (2×30 mL, 0.1 N). The organic layer was dried over anhydrous $Na_2SO_4$, filtered, and concentrated in vacuo. Purification was done using silica gel chromatography eluting with hexane: ethyl acetate (1:1) and fractions were combined and concentrated to afford the titled product as a white solid (1.06 g, 70%). HPLC: $R_t$ 2.58 min. (96.5% area). $^1$H NMR (400 MHz, $CDCl_3$), δ: 7.34 (t, J=7.6 Hz, 1H), 6.75 (d, J=7.6 Hz, 1H), 6.25 (d, J=8.1 Hz, 1H), 4.54 (s, 2H), 4.27 (bs, 2H), 0.84 (s, 9H), 0.11 (s, 6H); LRMS (ESI): m/z: 239.2.

iv. Preparation of N-[6-({[tert-butyl(dimethyl)silyl]oxy}methyl)pyridin-2-yl]4'-cyanobiphenyl-4-sulfonamide

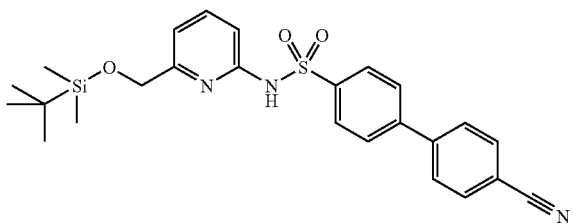

To a solution of dichloromethane (3 mL) was added 6-({[tert-butyl(dimethyl)silyl]oxy}methyl)pyridin-2-amine (0.15 g, 0.63 mmol), 4'-cyanobiphenyl4-sulfonyl chloride (0.18 g, 0.63 mmol) and pyridine (1.0 mL). The mixture was stirred for 3 hours then was washed with saturated sodium bicarbonate (2×30 mL) and aqueous hydrochloric acid (2×30 mL, 0.1 N). The organic layer was dried over anhydrous $Na_2SO_4$, filtered, and concentrated in vacuo. Purification was done using silica gel chromatography eluting with hexane: ethyl acetate (1:1) and combined fractions were concentrated to afford the above-titled intermediate as a white solid (0.21 g, 76%). HPLC: $R_t$4.236 min. (81% area). $^1$H NMR (400 MHz, $CDCl_3$), δ: 7.89 (d, J=8.3 Hz, 2H), 7.60 (d, J=8.3 Hz, 2H), 7.52-7.49 (m, 4H), 7.43 (t, J=7.6 Hz, 1H), 6.87 (d, J=8.6 Hz, 1H), 6.59 (d, J=7.3Hz, 1H), 6.22 (d, J=8.0 Hz, 1H), 4.55 (s, 2H), 0.82 (s, 9H), 0.05 (s, 6H); LRMS (ESI): m/z: 480.1.

v. Preparation of 4'-cyano-N-[6-(hydroxymethyl)pyridin-2-yl]biphenyl-4-sulfonamide To a solution of ethanol (5 mL) was added N-[6-({[tert-butyl(dimethyl)silyl]oxy}methyl)pyridin-2-yl]-4'-cyanobiphenyl-4-sulfonamide (0.21 g, 0.44 mmol) and aqueous hydrochloric acid (1.0 mL, 1 N). The mixture was stirred for 2 hours then diluted with ethyl acetate (40 mL). The mixture was washed with saturated sodium bicarbonate (2×30 mL) and aqueous hydrochloric acid (2×30 mL, 0.1 N). The organic layer was dried over anhydrous $Na_2SO_4$, filtered, and concentrated in vacuo. Purification was done using silica gel chromatography eluting with hexane: ethyl acetate (1:1), purified fractions were combined and concentrated. The residue was recrystallized from ethyl acetate and dried under vacuum to afford the above-titled product as an off white crystalline solid (0.13 g, 79%). HPLC: $R_t$ 2.450 min. (99.5% area). $^1$H NMR (400 MHz, $CD_3OD$), δ: 7.92 (d, J=8.6 Hz, 2H), 7.71-7.66 (m, 6H), 7.53 (t, J=8.1 Hz, 1H), 6.94 (d, J=8.6 Hz, 1H), 6.83 (d, J=8.1 Hz, 1H), 4.39 (s, 2H); HRMS (ESI): m/z: calcd'($C_{19}H_{16}N_3O_3S$): 366.0912; found: 366.0914.

METHOD C

Example 6

N-(6-amino-4-methylpyridin-2-yl)-4-chloro-2-fluoro-5-methylbenzenesulfonamide

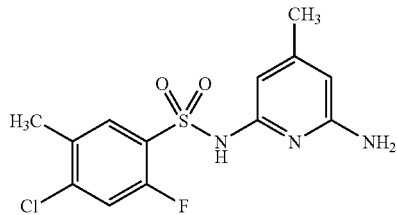

To a solution of tert-butyl (6-amino-4-methylpyridin-2-yl)carbamate (146 mg, 0.652 mmol, 1 equiv) in pyridine (3 mL) at 24° C. was added 4-chloro-2-fluoro-5-methylbenzenesulfonyl chloride (200 mg, 0.782 mmol, 1.2 equiv). After 24 h, the reaction mixture was concentrated in vacuo (~25 mm Hg). The residue was diluted with saturated aqueous ammonium chloride solution (10 mL), and the resulting solution was extracted with ethyl acetate (3×5 mL). The collected organic was dried over anhydrous sodium sulfate, filtered, and concentrated.

To a solution of the crude product in dichloromethane (3 mL) was added trifluoroacetic acid (1 mL) at 24° C. After 16 h, the reaction mixture was concentrated in vacuo (~25 mm Hg). Purification by high performance flash chromatography (0.5→3% methanol / dichloromethane) furnished the named compound (212 mg, 98%). $^1$H NMR (400 MHz, DMSO-$d_6$), δ: 12.00 (br s, 1H), 7.82 (d, J=7.8Hz, 1H), 7.49 (d, J=9.6 Hz, 1H), 6.51 (br s, 2H), 6.03 (s, 1H), 5.74 (s, 1H), 2.34 (s, 3H), 2.05 (s, 3H); Calculated for $C_{13}H_{14}N_3O_2$ClFS m/z: 330.0474. Found: 330.0470.

Example 7

N-(6-aminopyridin-2-yl)-4-butoxybenzenesulfonamide

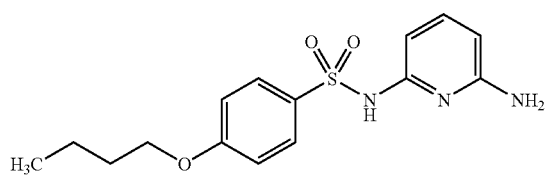

The 4-butoxylphenyl sulfonyl chloride (160 μmol, 2.0 eq, 400 μL of a 0.40 M in anhydrous pyridine) and tert-butyl (6-aminopyridin-2-yl)carbamate (80 μmol, 1.0 eq, 400 μL of a 0.20 M in anhydrous pyridine) was added into a test tube (75×10 mm, dried by heating at 110° C. for 16 h before use) equipped with a stir bar. The test tube was covered with Parafilm, and was stirred for 24 h at ambient temperature. The solvent (pyridine) was evaporated in vacuo. Trifluoroacetic acid (320 μL, 52.0 eq., excess, neat) was added into the test tube. The test tube was capped and vortexed for 5 h at ambient temperature. The excess TFA was removed in vacuo, and the residue was dissolved in DMSO (1.340 mL) and purified by HPLC. $^1$H NMR (500 MHz, DMSO-$d_6$) δ: 7.73 (d, J=7.7 Hz, 2H), 7.21 (t, J=7.2 Hz, 1H), 6.96 (d, J=6.9 Hz, 1H), 6.10 (d, J=6.1 Hz, 1H), 5.92 (d, J=5.9 Hz, 1H), 3.96 (t, J=6.6 Hz, 1H)), 1.64 (m, 2H), 1.37 (m, 2H), 0.87 (t, J=7.4 Hz, 3H). LRMS m/z: 322.0.

METHOD D

Example 8

4'-cyano-N-[6-(ethylamino)pyridin-2-yl]biphenyl4-sulfonamide

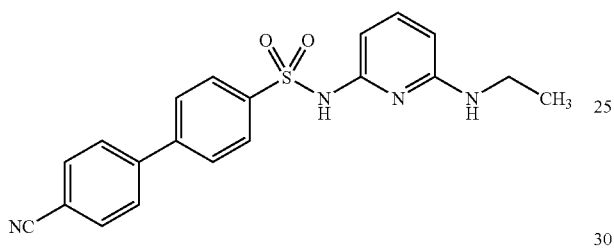

To a suspension of N-(6-Aminopyridin-2-yl)4'-cyanobiphenyl-4-sulfonamide (0.08 g, 0.23 mmol) in methanol (1 mL) was added acetaldehyde (0.02 mL, 0.34 mmol)) and molecular sieves (4 Å) were added. The resultant suspension was stirred for 30 minutes before the addition of sodium cyanoborohydride (0.043 g, 0.70 mmol). After 6 h, the reaction mixture was diluted with saturated aqueous sodium bicarbonate, and the aqueous layer was extracted with dichloromethane (2×10 mL). The combined organic layers was washed with brine and dried over sodium sulfate. Purification by high performance flash chromatography (25% EtOAc in hexanes) gave the product (0.055g, 63%). $^1$H NMR (400 MHz, CDCl$_3$), δ: 8.03 (d, J=8.6 Hz, 2H), 7.73 (d, J=8.6 Hz, 2H), 7.65 (d, J=8.6 Hz, 2H), 7.62 (d, J=8.6 Hz, 2H), 7.40 (t, J=8.3 Hz, 1H), 6.64 (d, J=8.1 Hz, 1H), 5.88 (d, J=8.3 Hz, 1H), 3.10-3.21 (m, 2H) 1.23 (t, J=7.2 Hz, 3H); LRMS (ESI) m/z: 379.12; Anal. Calcd for $C_{20}H_{18}N_4O_2S$: C, 63.47; H, 4.79; N, 14.80. Found: C, 63.11; H, 4.82; N, 14.63.

Additionally, the remaining Examples shown in Table 1, may be prepared by one of skill in the art following the methods as described in the Examples above using the appropriate starting materials.

TABLE 1

| Ex. No. | Structure | $K_i$ nm | % inh @ 0.1 uM | Mtd | $^1$H NMR | MS (m/z) |
|---|---|---|---|---|---|---|
| 1 | N-(6-amino-4-methylpyridin-2-yl)-2-(4-cyanophenyl)-4-methyl-1,3-thiazole-5-sulfonamide | 1.8 | 100 | A | (400 MHz, DMSO-$d_6$), δ: 12.08(br s, 1H), 8.09(d, J=8.3Hz, 2H), 7.95(d, J=8.3Hz, 2H), 6.62(br s, 2H), 6.12(s, 1H), 5.79(s, 1H), 2.59(s, 3H), 2.08(s, 3H) | 386.0745 |

TABLE 1-continued

| Ex. No. | Structure | $K_i$ nm | % inh @ 0.1 uM | Mtd | $^1$H NMR | MS (m/z) |
|---|---|---|---|---|---|---|
| 2(+) | (+)-4'-cyano-N-[6-(1-hydroxyethyl)pyridin-2-yl]biphenyl-4-sulfonamide | 19 | 85 | B | (400 MHz, CD$_3$OD), δ: 8.01(d, J=8.3, 2H), 7.96(t, J=8.1, 1H), 7.81(d, J=8.6Hz, 2H), 7.78-7.73(m, 4H), 7.21-7.16(m, 2H), 4.86(q, J=6.6Hz, 1H), 1.38(d, J=6.6Hz, 3H) | 380.1 |
| 2(−) | (−)-4'-cyano-N-[6-(1-hydroxypropyl)pyridin-2-yl]biphenyl-4-sulfonamide | NA | 53 | B | (400 MHz, CD$_3$OD), δ: 8.01(d, J=8.3, 2H), 7.96(t, J=8.1, 1H), 7.81(d, J=8.6Hz, 2H), 7.78-7.73(m, 4H), 7.21-7.16(m, 2H), 4.86(q, J=6.6Hz, 1H), 1.38(d, J=6.6Hz, 3H) | N/T |
| 3(−) | (−)-4'-cyano-N-[6-(1-hydroxypropyl)pyridin-2-yl]biphenyl-4-sulfonamide | NA | 59 | B | (400 MHz, CDCl$_3$), δ: 8.05(d, J=8.3Hz, 2H), 7.76(m, 2H), 7.58-7.71(m, 6H), 7.15(d, J=8.3Hz, 1H), 6.81(d, J=7.6Hz, 1H), 4.62(dd, J=7.2, 4.9Hz, 1H), 1.60-1.87(m, 2H), 0.89(t, J=7.5Hz, 3H) | N/T |
| 3(+) | (+)-4'-cyano-N-[6-(1-hydroxypropyl)pyridin-2-yl]biphenyl-4-sulfonamide | 5.19 | 97.9 | B | (400 MHz, CDCl$_3$), δ: 8.05(d, J=8.3Hz, 2H), 7.76(m, 2H), 7.58-7.71(m, 6H), 7.15(d, J=8.3Hz, 1H), 6.81(d, J=7.6Hz, 1H), 4.62(dd, J=7.2, 4.9Hz, 1H), 1.60-1.87(m, 2H), 0.89(t, J=7.5Hz, 3H) | N/T |
| 4(−) | (−)-4'-cyano-N-[6-(1-hydroxyethyl)pyridin-2-yl]-3-methylbiphenyl-4-sulfonamide | NA | 84 | B | (400 MHz, CDCl$_3$), δ: 8.19(d, J=8.1Hz, 1H), 7.70-7.77(m, 2H), 7.63-7.69(m, 2H), 7.57(t, J=8.0Hz, 1H), 7.46-7.53(m, 2H), 7.00(m, 1H), 6.81(m, 1H), 4.78(m, 1H), 2.78(s, 3H), 1.44(d, J=6.6Hz, 3H). | N/T |

TABLE 1-continued

| Ex. No. | Structure | $K_i$ nm | % inh @ 0.1 uM | Mtd | $^1$H NMR | MS (m/z) |
|---|---|---|---|---|---|---|
| 4(+) | (+)-4'-cyano-N-[6-(1-hydroxyethyl)pyridin-2-yl]-3-methylbiphenyl-4-sulfonamide | 2.7 | 100 | B | (400 MHz, CDCl$_3$), δ: 8.19(d, J=8.1Hz, 1H), 7.70-7.77(m, 2H), 7.63-7.69(m, 2H), 7.57(t, J=8.0Hz, 1H), 7.46-7.53(m, 2H), 7.00(m, 1H), 6.81(m, 1H), 4.78(m, 1H), 2.78(s, 3H), 1.44(d, J=6.6Hz, 3H). | N/T |
| 5 | N-(6-aminopyridin-2-yl)-4-chloro-2-fluoro-5-methylbenzenesulfonamide | 9.7 | 93 | B | (400 MHz, CDCl$_3$), δ: 7.80(d, J=7.6Hz, 1H), 7.42(t, J=8.3Hz, 1H), 7.08(d, J=9.4Hz, 1H), 6.83(d, J=8.3Hz, 1H), 6.00(d, J=8.3Hz, 1H), 5.91(s, 2H), 2.38(s, 3H) | 316.0322 |
| 6 | N-(6-amino-4-methylpyridin-2-yl)4-chloro-2-fluoro-5-methylbenzenesulfonamide | 2.8 | 98 | C | (400 MHz, DMSO-d$_6$), δ: 12.00(br s, 1H), 7.82(d, J=7.8Hz, 1H), 7.49(d, J=9.6Hz, 1H), 6.51(br s, 2H), 6.03(s, 1H), 5.74(s, 1H), 2.34(s, 3H), 2.05(s, 3H) | 330.0470 |
| 7 | N-(6-aminopyridin-2-yl)-4-butoxybenzenesulfonamide | 3.8 | 100 | C | (500 MHz, DMSO-d$_6$) δ: 7.73(d, J=7.7Hz, 2H), 7.21(t, J=7.2Hz, 1H), 6.96(d, J=6.9Hz, 1H), 6.10(d, J=6.1Hz, 1H), 5.92(d, J=5.9Hz, 1H), 3.96(t, J=6.6Hz, 1H), 1.64(m, 2H), 1.37(m, 2H), 0.87(t, J=7.4Hz, 3H) | 322.0 |
| 8 | 4'-cyano-N-[6-(ethylamino)pyridin-2-yl]biphenyl-4-sulfonamide | 4.8 | 88 | D | (400 MHz, CDCl$_3$), δ: 8.03(d, J=8.6Hz, 2H), 7.73(d, J=8.6Hz, 2H), 7.65(d, J=8.6Hz, 2H), 7.62(d, J=8.6Hz, 2H), 7.40(t, J=8.3Hz, 1H), 6.64(d, J=8.1Hz, 1H), 5.88(d, J=8.3Hz, 1H), 3.10-3.21(m, 2H) 1.23(t, J=7.2Hz, 3H) | 379.12 |

TABLE 1-continued

| Ex. No. | Structure | $K_i$ nm | % inh @ 0.1 uM | Mtd | $^1$H NMR | MS (m/z) |
|---|---|---|---|---|---|---|
| 9 | 4'-cyano-N-[6-(hydroxymethyl)pyridin-2-yl]biphenyl-4-sulfonamide | 2.8 | 100 | B | (400 MHz, CD$_3$OD(, δ: 7.92(d, J=8.6Hz, 2H), 7.71-7.66(m, 6H), 7.53(t, J=8.1Hz, 1H), 6.94(d, J=8.6Hz, 1H), 6.83(d, J=8.1Hz, 1H), 4.39(s, 2H) | 480.1 |

In Table 1, the term "min" refers to minutes; the term "MS" refers to mass spectroscopy; the term m/z refers the mass/charge ratio; the term "HPLC" refers to high performance liquid chromatography; the term "Ki" refers to activity against 11βHSD1 as measured by the assay as described above; and N/T refers to not tested.

TABLE 2

| Example No. | Structure | HEK EC$_{50}$ nM | Fa2N-4 nM |
|---|---|---|---|
| Comparative Example A* | 4'-Cyano-biphenyl-4-sulfonic acid [6-(2-hydroxy-ethyl)-pyridin-2-yl]-amide | 423 | 77.7 |
| 2(+) | (+)-4'-cyano-N-[6-(1-hydroxyethyl)pyridin-2-yl]biphenyl-4-sulfonamide | 160 | 56 |
| 3(+) | (+)-4'-cyano-N-[6-(1-hydroxypropyl)pyridin-2-yl]biphenyl-4-sulfonamide | 50.7 | 11.6 |

TABLE 2-continued

| Example No. | Structure | HEK EC$_{50}$ nM | Fa2N-4 nM |
|---|---|---|---|
| 4(+) | (+)-4'-cyano-N-[6-(1-hydroxyethyl)pyridin-2-yl]-3-methylbiphenyl-4-sulfonamide | 23.1 | 7.86 |
| 9 | 4'-cyano-N-[6-(hydroxymethyl)pyridin-2-yl]biphenyl-4-sulfonamide | 59 | 21.8 |

*Comparative Example A is Example 117 from WO2005-0148631A1.

Various embodiments of the present invention have been described above but a person skilled in the art realizes further minor alterations that would fall into the scope of the present invention. The breadth and scope of the present invention should not be limited by any of the above-described exemplary embodiments, but should be defined only in accordance with the following claims and their equivalents.

What is claimed is:

1. A compound of formula (I):

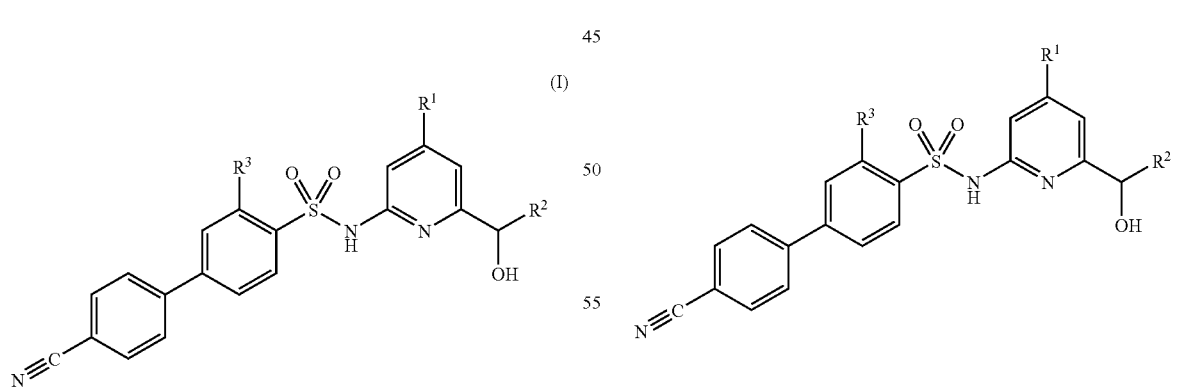

wherein
 $R^1$ is H or (C$_1$-C$_4$)alkyl;
 $R^2$ is H or (C$_1$-C$_4$)alkyl;
 $R^3$ is H, halo, (C$_1$-C$_6$)alkyl, or (C$_1$-C$_6$)alkoxy;
 or a pharmaceutically acceptable salt thereof.

2. The compound or pharmaceutically acceptable salt thereof according to claim 1, wherein $R^1$ is H.

3. The compound or pharmaceutically acceptable salt thereof according to claim 1, wherein $R^3$ is H or CH$_3$.

4. The compound or pharmaceutically acceptable salt thereof according to claim 1, wherein $R^2$ is —CH$_2$CH$_3$.

5. A compound of formula (I):

wherein
 $R^1$ is H or (C$_1$-C$_4$)alkyl;
 $R^2$ is H or (C$_1$-C$_4$)alkyl;
 $R^3$ is H, halo, (C$_1$-C$_6$)alkyl, or (C$_1$-C$_6$)alkoxy;
 or a pharmaceutically acceptable salt thereof, which is chiral.

6. The compound or pharmaceutically acceptable salt thereof according to claim 5, which is a (+) enantiomer.

7. A compound selected from the group consisting of:

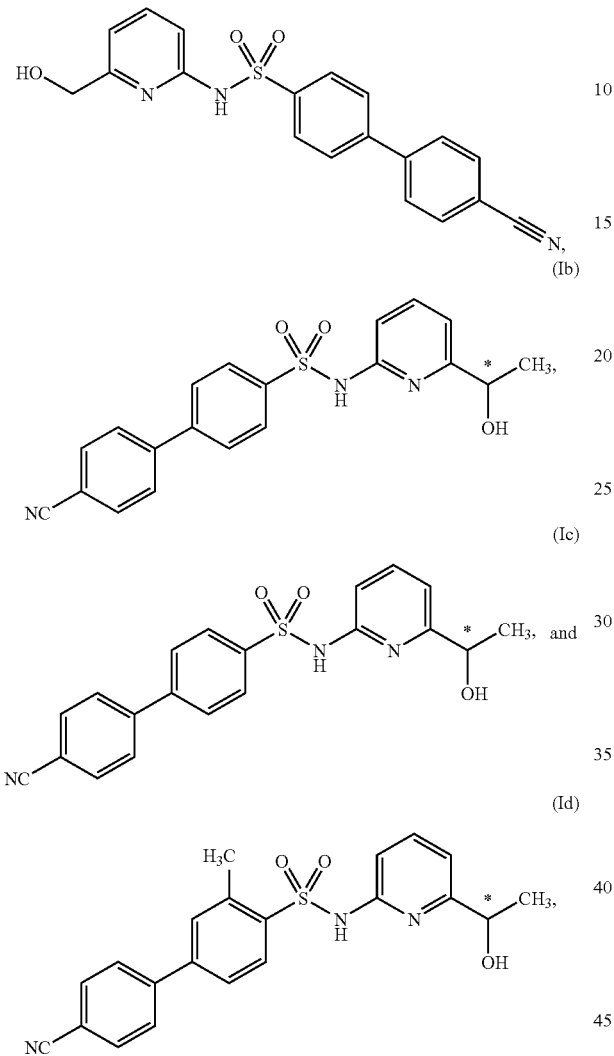

or pharmaceutically acceptable salt thereof wherein the symbol "*" represents a chiral center.

8. The compound of formula (Ib), (Ic), (Id), or pharmaceutically acceptable salt thereof according to claim 7, which is a (+) enantiomer.

9. A compound having the formula (II):

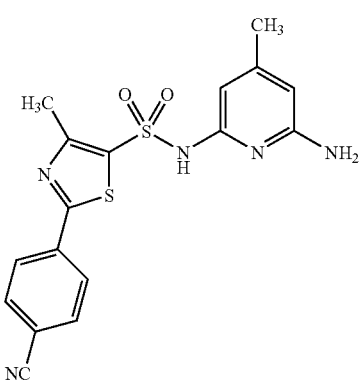

or a pharmaceutically acceptable salt thereof.

10. A pharmaceutical composition comprising an effective amount of a compound or a pharmaceutically acceptable salt thereof according to claim 1 and a pharmaceutically acceptable carrier.

11. A pharmaceutical composition comprising an effective amount of a compound or a pharmaceutically acceptable salt thereof according to claim 9, and a pharmaceutically acceptable carrier.

* * * * *